(12) United States Patent
Koentgen et al.

(10) Patent No.: US 6,521,741 B1
(45) Date of Patent: *Feb. 18, 2003

(54) CATALYTIC ANTIBODIES AND A METHOD OF PRODUCING SAME

(75) Inventors: Frank Koentgen, Lower Templestowe (AU); Gabriele Maria Suess, Lower Templestowe (AU); David Mathew Tarlinton, Blackburn (AU); Herbert Rudolf Treutlein, Moonee Ponds (AU)

(73) Assignee: Frank Koentgen Pty Ltd., Lower Templestowe (AU)

( * ) Notice: Subject to any disclaimer, the term of this patent is extended or adjusted under 35 U.S.C. 154(b) by 0 days.

This patent is subject to a terminal disclaimer.

(21) Appl. No.: 09/710,299

(22) Filed: Nov. 9, 2000

Related U.S. Application Data

(62) Division of application No. 09/160,567, filed on Sep. 25, 1998, now Pat. No. 6,326,179, which is a division of application No. 08/828,741, filed on Mar. 26, 1997, now Pat. No. 6,043,069.

(30) Foreign Application Priority Data

Mar. 26, 1996 (AU) ............................................. 8951/96
Feb. 27, 1997 (AU) ............................................. 5375/97

(51) Int. Cl.$^7$ .......................... C07K 14/00; C07K 2/00; C12N 9/00
(52) U.S. Cl. ........................ 530/350; 514/2; 435/188.5
(58) Field of Search ..................... 435/188.5; 530/350; 514/2

(56) References Cited

U.S. PATENT DOCUMENTS

| | | | |
|---|---|---|---|
| 4,888,281 A | 12/1989 | Schochetman et al. | ....... 435/72 |
| 4,900,674 A | 2/1990 | Benkovic et al. | ............ 435/232 |
| 5,126,258 A | 6/1992 | Lerner et al. | ............. 435/188.5 |
| 5,187,086 A | 2/1993 | Janda et al. | ................. 435/146 |
| 5,190,865 A | 3/1993 | Schultz | ........................ 435/108 |
| 5,219,732 A | 6/1993 | Schultz | ........................ 435/41 |
| 5,302,516 A | 4/1994 | Schultz | ........................ 435/41 |
| 5,439,812 A | 8/1995 | Benkovic et al. | ............ 435/109 |

FOREIGN PATENT DOCUMENTS

WO 93/22342 11/1993

OTHER PUBLICATIONS

Janda, K.D., et al. (1991) Tetrahedron 47 (14/15), 2503–2506.

Kihlberg, B.M., et al. (1992) J. Biol. Chem. 267(35), 25583–25588.

Kastern, W., et al. (1992) J. Biol. Chem. 267(18), 12820–12825.

*Primary Examiner*—Charles L. Patterson, Jr.
(74) *Attorney, Agent, or Firm*—Scully, Scott, Murphy & Presser

(57) ABSTRACT

The present invention is directed generally to catalytic antibodies and, more particularly, to a novel method of producing same. The method of the present invention is predicated in part on the exploitation of the products of catalysis to induce B cell mitogenesis. In a preferred embodiment, a growth factor having an ability to induce B cell mitogenesis is linked to a target antigen to which catalytic antibodies are sought. B cell mitogenesis is then dependent on the catalytic cleavage of the antigen portion of the growth factor by catalytic antibodies on the surface of B cells. The method of the present invention is useful for generating catalytic antibodies for both therapeutic and diagnostic purposes.

20 Claims, 24 Drawing Sheets

CATALYTIC ANTIBODIES AND A METHOD OF PRODUCING SAME

CROSS REFERENCE TO RELATED APPLICATIONS

Figure 1:
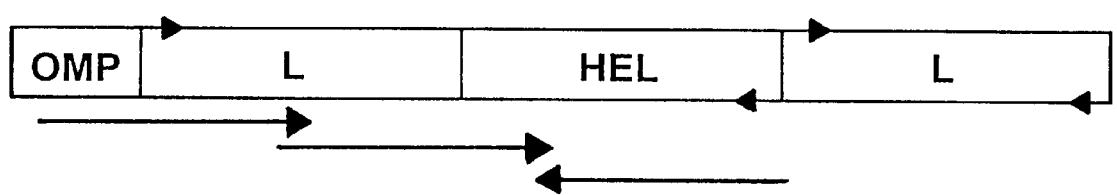

The present application is a divisional of Ser. No. 09/160,567, filed Sep. 25, 1998, now U.S. Pat. No. 6,328,179, which is a divisional of application Ser. No. 08/828,741 filed Mar. 26, 1997, now U.S. Pat. No. 6,043,069.

The present invention is directed generally to catalytic antibodies and, more particularly, to a novel method of producing same. The method of the present invention is predicated in part on the exploitation of the products of catalysis to induce B cell mitogenesis. In a preferred embodiment, a growth factor having an ability to induce B cell mitogenesis is linked to a target antigen to which catalytic antibodies are sought. B cell mitogenesis is then dependent on the catalytic cleavage of the antigen portion of the growth factor by catalytic antibodies on the surface of B cells. The method of the present invention is useful for generating catalytic antibodies for both therapeutic and diagnostic purposes.

Sequence Identity Numbers (SEQ ID NOs.) for the nucleotide and amino acid sequences referred to in the specification are defined following the Examples.

Throughout this specification, unless the context requires otherwise, the word "comprises", or variations such as "comprises" or "comprising", will be understood to imply the inclusion of a stated element or integer or group of elements or integers but not the exclusion of any other element or integer or group of elements or integers.

The rapidly increasing sophistication of recombinant DNA technology is greatly facilitating research and development in the medical and allied health fields. A particularly important area of research is the use of recombinant antigens to stimulate immune response mechanisms and outcomes. However, until now, recombinant techniques have not been particularly effective in the generation of catalytic antibodies.

Catalytic antibodies are highly substrate specific catalysts which can be used, for example, to proteolytically activate or inactivate proteins. Catalytic antibodies have great potential a therapeutic agents in human diseases such as rheumatoid arthritis, AIDS and Alzhiemer's disease amongst many others.

Antibody therapy is already routinely used in patients. Antibodies have a half-life of about 23 days in the circulation of humans which is a clear advantage over other drugs. Catalytic antibodies, however, are considered to be even more effective. They are recycled after their antigenic encounter and are not bound to the antigen as occurs with "classical" antibodies. Catalytic antibodies should, therefore, function at a much lower dose than classical antibodies and could be used at sub-immunogenic doses. Catalytic antibodies would be particularly useful in long term therapy.

Traditionally, catalytic antibodies have been generated by immunising mice with transition state analogs. Such antibodies have been shown to catalyse several chemical reactions. However, this approach has a severe limitation in that it is difficult to predict the structure of transition state analogs which effect proteolysis of specific proteins. Immunising a mouse with a transition state analog is by definition inefficient since it selects B cells on the ability of surface immunoglobulins to bind the analogs and not on the catalytic activity of the surface immunoglobulins. This is one of the reasons why catalytic antibodies have relatively low turn-over rates and cannot compete with the naturally occurring enzyme counterparts. As a consequence, catalytic antibodies have not previously achieved prominence as therapeutic or diagnostic tools.

There is a need, therefore, to develop a more efficacious approach to generating catalytic antibodies having desired catalytic specificity. In accordance with the present invention, the inventors have developed such an approach based on a recombinant or a synthetic growth factor having an ability to induce B cell mitogenesis. A precursor form of the growth factor selects "catalytic" B cells. The present invention provides, therefore, for the exploitation of the products of catalysis for B cell activation which may and can be antigen binding site independent.

Accordingly, one aspect of the present invention is directed to a recombinant or synthetic growth factor or a precursor thereof comprising a B cell surface molecule binding portion wherein said growth factor or a catalytic product of said precursor is capable of inducing B cell mitogenesis.

More particularly, the present invention provides a recombinant or synthetic growth factor comprising a B cell surface molecule binding portion wherein said growth factor induces B cell mitogenesis.

In one aspect of the present invention, the recombinant or synthetic growth factor comprises a B cell surface molecule binding portion and a portion providing T cell dependent help for a B cell such that said growth factor induces B cell mitogenesis.

In another aspect, the portion providing T cell dependent help for a B cell is supplied independently of the growth factor. An example of an exogenously supplied portion having T cell dependent help for a B cell is anti-CD40 antibodies or functional equivalents thereof.

In a particularly preferred embodiment, the B cell surface molecule binding portion comprises a B cell surface immunoglobulin binding portion although the present invention extends to a range of B cell surface molecules the binding, interaction and/or cross-linking thereof leads to or facilitates B cell mitogenesis. Reference hereinafter to a "B cell surface molecule" includes reference to a B cell surface immunoglobulin. The portion providing T cell dependent help for a B cell is preferably but not exclusively a T cell epitope. Reference hereinafter to a portion providing T cell dependent help for a B cell includes a T cell epitope.

The present invention further contemplates a composition of matter capable of inducing B cell mitogenesis said composition of matter comprising components selected from:

(i) a recombinant or synthetic molecule comprising a B cell surface molecule binding portion;

(ii) a recombinant or synthetic molecule in multimeric form comprising a B cell surface molecule binding surface molecule binding portion;

(iii) a recombinant or synthetic molecule of (i) or comprising a further portion providing T cell dependent help for a B cell; and (iv) separate compositions mixed prior to use or used sequentially or simultaneously comprising in a first composition a component having a B cell surface molecule binding portion and in a second composition a molecule capable of providing T cell dependent help for a B cell.

Preferably, the molecule capable of providing T cell dependent help for a B cell is a T cell epitope or is an anti-CD40 antibody or functional equivalents thereof.

Preferably, to ensure cross-liking of B cell surface molecules to induce blastogenesis, the growth factor comprises at least two B cell surface molecule binding portions. Alternatively, where the growth factor is present in multimeric form, the molecule may comprise a single B cell surface molecule binding portion.

Even more preferably, the growth factor comprises a T cell epitope portion flanked by, adjacent to or proximal with at least one B cell surface molecule-binding portion. The presentation of a T cell epitope on the surface of a B cell allows for B cell mitogenesis. The term "B cell mitogenesis" is used herein in its broadest context and includes B cell activation, clonal expansion, affinity maturation and/or antibody secretion as well as growth and differentiation. The term "mitogenic" as used herein means "mitogenesis".

In another embodiment, the recombinant or synthetic growth factor comprises a further portion permitting multimerisation of the growth factor. A multimer comprises two or more growth factor molecules or a precursor thereof. Examples of portions inducing multimerisation include but are not limited to an antibody, a region facilitating formation of cross-linked molecules or a signal peptide. Cross-linkage in this context includes any interaction that provides bonding adequate to lead to multimer formation including but not limited to covalent linkage, ionic linkage, lattice association, ionic bridges, salt bridges and non-specific molecular association. A particularly preferred embodiment of the present invention is directed to the use of a signal peptide such as the signal peptide of the Outer Membrane Portion A (ompA) [Skerra, *Gene*, 151: 131–135, 1994] or a functional derivative thereof A "functional derivative" in this context is a mutant or derivative of the ompA signal peptide (or its functional equivalent) which still permits multimer formation of the growth factor.

In a preferred embodiment, where the B cell surface molecule is an immunoglobulin, the B cell surface binding portion of the growth factor generally binds to part of an immunoglobulin such as the variable portion of a heavy or light chain of an immunoglobulin.

An example of an immunoglobulin binding molecule is protein L from *Peptostreptococcus magnus*. Protein L has five immunoglobulin-binding domains. Other immunoglobulin binding molecules include protein A, protein G and protein H. The present invention, however, extends to any molecule capable of binding to a B cell surface component including, for example, a ligand of a B cell receptor.

The portion of the recombinant or synthetic molecule defining a T cell epitope is presented to a preferably already primed T cell to induce B cell proliferation and affinity maturation of an antibody in the germinal centre. This is generally accompanied by immunoglobulin class switching and antibody secretion into the serum. Generally, the T cell epitope is internalised within the B cell and presented on major histocompatbility complex (MHC) class II.

In a particularly preferred embodiment, the T cell epitope is from hen egg lysozyme (HEL) [Altavia et al, *Molecular Immunology,* 31: 1–19, 1994] or is a derivative thereof such as a peptide comprising no acids 42 to 62 from HEL or a homologue or analog thereof. This T cell epitope is recognised by the T cell receptor (TCR) of HEL specific T cells when presented by an antigen presenting cell (APC) on the MHC class II molecule H-$2A^K$ in mice or other MHC class II molecules or their equivalents in other mammals such as humans. Examples of other T cell epitopes include but are not limited to tetanus toxoid, ovalbumin, malarial antigens as well as other regions of HEL. One skilled in the art would readily be able to select an appropriate T cell epitope.

In an alternative embodiment, the portion providing T cell dependent help of a B cell is not a T cell epitope in the classical sense but is nevertheless able to function in a similar manner. An example of such a portion is an anti-CD40 antibody.

Another aspect of the present invention contemplates a recombinant or synthetic molecule having the structure:

$$X_1X_2X_3$$

wherein:

$X_1$ and $X_3$ may be the same or different and each is a B cell surface molecule binding entity;

$X_2$ is a portion providing T cell dependent help for a B cell; and wherein the recombinant or synthetic molecule is capable of inducing T cell dependent B cell mitogenesis of the B cell which $X_1$ and $X_3$ bind.

The representation $X_1X_2X_3$ is not to be taken as imposing any sequential constraints and the present invention covers any sequence comprising the elements $X_1X_2X_3$ such as $X_1X_3X_2$, $X_3X_2X_1$, $X_2X_3X_1$, $X_2X_1X_3$, and $X_3X_1X_2$.

The present invention further provides a recombinant or synthetic molecule having the structure:

$$X_1X_2X_3$$

wherein:

$X_1$ and $X_3$ may be the same or different and each is a B cell surface immunoglobulin binding entity;

$X_2$ is a T cell epitope; and wherein the recombinant or synthetic molecule is capable of inducing T cell dependent B cell mitogenesis of the B cell to which $X_1$ and $X_3$ bind.

The present invention yet further provides a recombinant or synthetic molecule having the structure:

$$MX_1[X_2]_b$$

wherein:

$X_1$ is a B cell surface molecule binding entity such as a B cell surface immunoglobulin binding entity;

$X_2$ is a portion providing T cell dependent help for a B cell;

M is a portion enabling or facilitating multimer formation of the recombinant or synthetic molecule; and b represents the number of $X_2$ molecules and may be 0, 1 or >1.

An example of M is a signal peptide such as from ompA. The multimeric effect of M is to provide a molecule $[MX_1[X_2]_b]_k$ where M, $X_1$, $X_2$ and b are as defined above and k is 1 or >1. An example of k is from about 2 to about 1000 and more preferably from above >1 to about 50–200.

The optional nature of $X_2$ may alternatively relate to $X_1$. The molecular components of $MX_1[X_2]_b$ may be in any order.

Preferably, but not exclusively $X_1$ is derived from the L protein from *P. magnus.*

Preferably, $X_2$ is a T cell epitope derived from HEL such as but not limited to amino acids 42 to 62 from HEL. In an alternative embodiment, where b=0 $X_2$ is not a T cell epitope and is exogenously supplied facilitating T cell dependent help for a B cell. In this case, $X_2$ may be, for example, an anti-CD40 antibody.

In a particularly preferred embodiment, $X_1X_2X_3$ as defined above is referred to herein as "LHL" where L is an immunoglobulin binding entity from L protein from *P. magnus* and H corresponds to amino acids 42 to 62 from HEL or an equivalent thereof. The nucleotide and amino acid sequences of LHL are shown in SEQ ID NO:1 and SEQ ID NO:2, respectively.

The present invention extends to a growth factor or precursor thereof having the amino acid sequence set forth in SEQ ID NO:2 or an amino acid sequence having at least 60% similarity thereto (excluding the amino acid sequence of an antigen) or an amino acid sequence encoded by nucleotide sequence set forth in SEQ ID NO:1 or a nucleotide sequence capable of hybridizing to SEQ ID NO:1 under low stringency conditions.

Reference herein to a low stringency at 42° C. includes and encompasses from at least about 1% v/v to at least about 15% v/v formanide and from at least about 1M to at least about 2M salt for hybridisation, and at least about 1M to at least about 2M salt for washing conditions, Alternative stringency conditions may be applied where necessary, such as medium stringency, which includes and encompasses from at least about 16% v/v to at least about 30% v/v formamide and from at least about 0.5M to at least about 0.9M salt for hybridisation, and at least about 0.5M to at least about 0.9M salt for washing conditions, or high stringency, which includes and encompasses from at least about 31% v/v to at least about 50% v/v formamide and from at least about 0.01M to at leas. about 0.15M salt for hybridisation, and at least about 0.01M to at least about 0.15M salt for washing conditions.

The two "L" domains from protein L linked by the "H" domain from HEL build the growth factor LHL which crosslinks the surface immunoglobulin on B cells. This cross-linking induces B cell activation and blast formation, The internalisation and processing of LHL leads to the presentation of H on MHC II. T cell recognition of MHC II with the H peptide signals the activated B cell to proliferate and undergo antibody class switching and secretion.

The mitogenic growth factor of the present invention is most useful in generating antibodies of desired catalytic specificity when in a precursor form which selects "catalytic" B cells. A precursor growth factor comprises a target antigen to which a catalytic antibody is sought and which mask antigen-independent clonal expansion of B cells. Upon cleavage of the antigen by a selected B cell surface immunoglobulin, the growth factor can induce B cell mitogenesis.

In effect, then B cells are selected on the catalytic activity of their surface immunoglobulin rather than on their binding to a transition state analog. This allows for affinity maturation in the germinal centres and ensures "catalytic-maturation" to obtain the highest enzymatic turn-over rate possible in vivo. This aspect of the present invention is achieved by designing a B cell growth factor precursor comprising $X_1X_2X_3$ as defined above, such as LHL, shielded and substantially inactive until released through cleavage by a catalytic antibody on a B cell surface. The term "cleavage" in this context is not limiting to the breaking of bonds but includes interaction adequate to remove or reduce shielding of the B cell growth factor.

The liberated $X_1X_2X_3$ activates the catalytic B cell by crosslinking the B cell surface molecules such B cell surface immunoglobulins via the $X_1X_3$ domains. $X_1X_2X_3$ is then internalised and processed analogous to a normal antigen. Intracellular processing generates the T cell epitope $X_2$ incorporated in $X_1X_2X_3$. The presentation of $X_2$ on the B cell surface leads to T cell dependent clonal expansion of the B cell as well as catalytic maturation and secretion of the catalytic antibody. The catalytic antibodies can then be detected in serum and catalytic B cells can be recovered by standard techniques.

According to this aspect of the present invention, there is provided a recombinant or synthetic growth factor precursor comprising an antigen linked or otherwise associated with a growth factor capable of inducing B cell mitogenesis, wherein the products of catalysis of said growth factor precursor permit B cell mitogenesis which may and can be antigen binding site independent.

According to another aspect of the present invention, there is provided a recombinant or synthetic growth factor precursor comprising an antigen linked to or otherwise associated with a B cell surface binding molecule portion and a portion providing T cell dependent help to a B cell such that upon cleavage of said antigen or of a region proximal to said antigen, said B cell surface molecule portion and said T cell dependent help portion form a growth factor which induces B cell mitogenesis.

Preferably, the present invention is directed to a recombinant or synthetic growth factor precursor comprising an antigen linked to or otherwise associated with a B cell surface immunoglobulin binding portion and a T cell epitope portion such that upon cleavage of said antigen or of a region proximal to said antigen, said B cell surface immunoglobulin and T cell epitope form a growth factor having B cell mitogenic properties.

In an alternative embodiment, the present invention provides a recombinant or synthetic growth factor precursor comprising an antigen linked to or otherwise associated with a B cell surface molecule binding portion and a portion conferring a multimeric form of said growth factor precursor when cleavage of said antigen or of a region proximal to said antigen provides a growth factor comprising a B cell surface molecule binding portion having the ability to induce B cell mitogenesis.

The antigen according to this aspect of the present invention is any antigen to which a catalytic antibody is sought. Examples include cytokines such as but not limited to tumor necrosis factor (TNF), an interleukin (IL) such as IL-1 to IL-15, interferons (IFN) such as IFNα, IFNβ or IFNγ, colony-stimulating factors (CSF) such as granulocyte colony-stimulating factor (G-CSF), granulocyte-macrophase colony-stimulation factor (GM-CSF), blood factors such as Factor VIII, erythropoietin and haemopoietin, cancer antigens, docking receptors from pathogenic viruses such as HIV, influenza virus or a hepatitis virus (eg. HEP A, HEP B, HEP C or HEP E) and amyloid plaques such as in Alzheimer's disease patients or myeloma patients. More particularly, in the case of TNF, proteolytic inactivation of TNF would be useful in the treatment of rheumatoid arthritis and toxic shock syndrome. By targeting viral docking receptors, pathogenic viruses such as HIV, hepatitis viruses and influenza viruses are rendered effectively inactive. Catalytic antibodies will also be useful in the clearance of amyloid plaques in Alheimer's disease or myeloma disease patients. Targeting IgE, for example, may provide a mechanism for treating inflammatory conditions such as asthma.

The catalytic antibodies of the present invention may also be useful in detoxifying drugs such as drugs consumed by an individual. For example, the effects of cannabis or heroin or other drugs could be treated in an individual by the administration of catalytic antibodies directed to the active components of those drugs. Furthermore, catalytic antibodies may be useful in the treatment of autoimmune and inflammatory disease conditions such as by targeting autoimmune antibodies. Catalytic antibodies also have a use in environmental situations and could be directed to environmental pollutants such as petroleum products and plastics. In all these situations, suitable antigens would be selected and incorporated into the growth factor precursor of the present invention.

In a related aspect of the present invention, the "antigen" portion of the growth factor precursor can be mimiced by a target site such as an amino acid linker sequence comprising a protease cleavage site. Examples include an amino acid linker sequence comprising the tabacco etch virus (TEV) protease cleavage site More particularly, in the case of a TEV protease cleavage site, cleaving of the amino acid linker sequence by the TEV protease would be useful for producing characteristics similar to those of a catalytic antibody. This provides a useful model system for developing growth factor molecules.

Another aspect of the present invention provides a recombinant or synthetic molecule having the structure:

$$AX_1X_2X_3A$$

wherein
A is a target antigen for which a catalytic antibody is sought;
$X_1$ and $X_3$ may be the same or different and each is a B cell surface molecule binding entity;
$X_2$ is a portion providing T cell dependent help for a catalytic B cell;
wherein a catalytic antibody on the surface of said B cell is capable of cleaving all or part of A from said recombinant or synthetic molecule resulting in the molecule $[A']X_1X_2X_3[A']$ wherein A' is optionally present and is a portion of A after cleavage with the catalytic antibody and wherein said resulting molecule is capable of inducing T cell dependent clonal expansion of the B cell to which $X_1$ and $X_3$ bind.

The $AX_1X_2X_3A$ molecule may be in any sequence order.

Anther aspect of the present invention is directed to a recombitant or synthetic molecule having the structure:

$$[M]_c AX_1[X_2]_d[X_3]_e A[M]_f$$

wherein:
A is a target antigen for which a catalytic antibody is sought;
$X_1$ and $X_3$ may be the same or different and each is a B cell surface molecule binding entity;
$X_2$ is a portion providing T cell dependent help for a B cell;
M is a portion enabling or facilitating multimer formation of the recombinant or synthetic molecule;
c and f may be the same or different and each is 0, 1 or >1;
e is 0 or 1 with the proviso then if both c and f are 0 then e cannot be 0;
d is 0 or 1 or >1;
wherein a catalytic antibody on the surface of said B cell is capable of cleaving all or a portion of A from said recombinant or synthetic molecule and a resulting catalytic product is capable of inducing B cell mitogenesis.

The growth factor precursor enables an antigen to be recognised by a B cell via a growth factor capable of inducing B cell mitogenesis. The antigen effectively masks B cell activation without prior catalytic activation. The growth factor is in "precursor" form, therefore, until cleavage of all or part of the antigen. A further masking may also be provided by molecules capable of binding to or otherwise associating with the B cell surface molecule binding domains of the B cell surface molecule binding portion. Examples of suitable masking molecules include but are not limited to the variable portion of a kappa or lambda light chain of an immunoglobulin.

Alternatively, a fragment comprising a variable heavy and light chain (Fv) may be employed which is preferably but not exclusively a single chain (sc) and/or disulfide stabilized (ds). The nucleotide and corresponding amino acid sequences for the variable portion of kappa light chain are shown in SEQ ID NO:10 and SEQ ID NO:11, respectively.

Notwithstanding that the abovementioned immunoglobulin portions are usefull molecules for blocking B cell surface immunoglobulin binding domains, other molecules may also be used. For example, natural product screening would very readily identify molecules from natural sources such as coral, soil, plants, ocean beds, marine invertebrates or from other convenient sources which would bind to immunoglobulin binding domains of L protein or other B cell surface binding molecules.

In a particularly preferred embodiment, the recombinant or synthetic growth factor precursor substantially prevents binding of $X_1$ and $X_3$ to their cognate B cell surface molecules thereby preventing B cell activation by having immunoglobulin peptides or chemical equivalents thereof or other B cell surface molecule blocking reagents linked, fused or otherwise associated with the growth factor to facilitate masking of the B cell activating effects of the growth factor. In a particularly preferred embodiment, the precursor comprises an antigen to which a catalytic antibody is sought and portions capable or masking the B cell surface molecule binding domains of the B cell surface molecule binding portion or the growth factor. The precursor may contain variable kappa or lambda light chain domains or an sc-ds-Fv molecule or masking molecules detected following natural product screening.

Generally, the immunoglobulin molecules which bind to the B cell surface immunoglobulin binding portion as a growth factor are linked to the N-terminal and C-terminal portions respectively of the antigen flanking the growth factor. For example, one particularly preferred embodiment of the present invention provides a growth factor precursor comprising the structure:

$$I'AX_1X_2X_3AI''$$

wherein:
I' and I" are optionally present and may be the same or different and each is a blocking reagent for $X_1$ and $X_3$ such as a kappa or lambda light chain or a sc-ds-Fv molecule;
A is the target antigen for which a catalytic antibody is sought;
$X_1$ and $X_3$ are B cell surface molecule binding entities; and
$X_2$ is an entity providing T cell dependent help to a B cell.
Wherein a catalytic antibody on the surface of said B cell is capable of cleaving all or part of A from said recombinant or synthetic molecule resulting in the molecule $[A']X_1X_2X_3[A']$ wherein A' is optionally present and is a portion of A after cleavage with the catalytic antibody wherein said resulting molecule is capable of inducing T cell dependent B cell mitogenesis of the B cell to which $X_1$ and $X_3$ bind.

The molecular components of $I'AX_1X_2X_3AI''$ may be in any sequence order.

The present invention extends to $X_1$ and $X_3$ being any B cell surface molecule binding molecules and components I' and I" block or mask the binding of such molecules to the B cell surface molecules.

In another embodiment the I'A $X_1X_2X_3$A I" molecule or part thereof may be in multimeric form, This is particularly the case when all or part of the molecule includes a multi-merisation component (M) such as but not limited to the signal peptide of ompA. The monomeric units may be bound or otherwise associated together by any number of binding means such as contemplated above including covalent bonding, salt bridges, disulfide bridges and hydrophobic interactions amongst many others. Depending on the extent of multimerisation, this may impair the masking ability of B cell surface molecule binding domains of the growth factor and some antigen-independent clonal expansion may occur. This may not be too disadvantageous where there is at least some catalytic antibody dependent B cell mitogenesis.

According to this embodiment, there is provided a growth factor precursor comprising the structure:

$$[I'AX_1[X_2']_o[X_2X_3AI"]_n]_m$$

wherein:
I' and I" may be the same or different and each is a blocking reagent for $X_1$ and $X_3$ such as a kappa or lambda light chain or an sc-ds-Fv;
A is the target antigen for which a catalytic antibody is sought;
$X_1$ and $X_3$ are B cell surface molecule binding entities;
$X_2$ and $X_2'$ may be the same or different and each is an entity capable or providing T cell dependent help for a B cell;
o may be 0 or 1;
n indicates the multimeric nature of the component in parentheses and may be 0, 1 or >1;
m indicates the multimeric nature of the component in parenthesis and may be 1 or >1.

Preferably, n and m are each from about 1 to about 10,000 more preferably from about 1 to about 1,000 and still more preferably from about 1 to about 200.

Preferably, if n is 0, then o is 1.

In alternative embodiments, the growth factor precursor comprises the structure $[[I'AX_2X_3]_n[X_2']_o[X_1AI"]_m$ or $[[I'AX_1[X_2']_o]_n[X_2X_3AI"]_m]$.

The exact number ascribed to n and m may not be ascertainable but the multimeric nature identified functionally or physically by size (eg. determined using HPLC or PAGE).

Examples of A include but are not limited to those hereinbefore described.

The present invention extends to the substitution of a non-antigen cleavage site such as a protease sensitive peptide which provides a useful model for designing growth factor molecules.

An exemplified growth actor precursor of the present invention is referred to herein as "CATAB" and comprises a TNF flanked LHL with the variable region from a kappa and/or lambda light chain further masking the B surface immunoglobulin binding domain of the L molecules.

In another embodiment, the growth factor precursor mimics a CATAB being activatable by means other than or in addition to a catalytic antibody. For example, an enzyme sensitive molecule may be the "antigen". In one embodiment, the CATAB mimic is referred to herein as "TLHL" and comprises a variable kappa light chain linked to the N-terminus of an amino acid linker sequence comprising the TEV protease cleavage site which is in turn linked to LHL. The nucleotide and amino acid sequences for TLHL are shown in SEQ ID NO:5 and SEQ ID NO:6. In another embodiment, the TLHL further comprises another amino acid linker sequence comprising the TEV protease cleavage site and a variable kappa light chain linked to the C-terminus of the latter amino acid linker sequence and is referred to herein as CATAB-TEV. The nucleotide sequence and corresponding amino acid sequence of CATAB is shown in SEQ ID NO:3 and SEQ ID NO:4, respectively.

The present invention extends to a growth factor precursor comprising a sequence of amino acids selected from:
(i) the amino acid sequence set forth in SEQ ID NO:4 or having at least 60% similarity thereto (excluding the amino acid sequence of an antigen);
(ii) an amino acid sequence encoded by the nucleotide sequence set forth in SEQ ID NO:3 or a nucleotide sequence having at least 60% similarity to the nucleotide sequence set forth in SEQ ID NO:3;
(iii) an amino acid sequence encoded by a nucleotide sequence capable of hybridizing to SEQ ID NO:3 under low stringency conditions wherein catalytic properties of said growth factor precursor are capable of inducing B cell mitogenesis.

The variable kappa light chain portions may conveniently be derived from the Bence Jones protein LEN, which has been shown to bind to certain immunoglobulin binding proteins such as L. Alternatively, an Fv may be used such as a sc-ds-Fv.

Upon cleavage of the growth factor precursor CATAB by a catalytic antibody recognising the antigen (for example, a TNF peptide portion), the covalent linkage between the L domains and the variable kappa light chains is broken. The blocking variable kappa light chains will dissociate from the L domains due to the relatively low affinity ($\sim 10^{-7}$M) of individual domains for each other. This will release the mature growth factor LHL which can bind to and crosslink the surface immunoglobulin with an affinity of $10^{-9}$M. A similar mechanism operates where molecules other than variable kappa light chains, TNF, L and H are employed.

This B cell surface immunoglobulin crosslinking activates the B cell and induces the down stream events that lead to catalytic maturation and secretion of the catalytic antibody. Catalytic antibodies can be detected in the serum using any number of procedures such as ELISA based assays and catalytic B cells may be recovered with standard hybridoma technology. Where the catalytic antibodies are from non-human animals, these can be humanised by recombinant DNA technology and produced for therapeutical applications in humans. Alternatively, the antibodies may be generated in a "humanized" animal such as a humanized mouse which is transgenic for the human Ig loci.

The present invention contemplates derivatives of the growth factor and/or its precursor. A derivative includes a mutant, part, fragment, portion, homologue or analogue of the growth factor and/or precursor or any components thereof. Derivatives to amino acid sequences include single or multiple amino acid substitutions, deletions and/or additions. For example, derivatives of SEQ ID NO:2 or SEQ ED NO:4 include sequences having at least 60% similarity thereto (excluding amino acid sequence of antigen) or which are encoded by a nucleotide sequence capable of hybridizing in SEQ ID NO:1 or SEQ ID NO:3 under low stringency conditions.

Particularly useful derivatives include chemical analogues of the growth factor and/or its precursor or components thereof. Such chemical analogues may be useful in stabilizing the molecule for therapeutic or diagnostic use.

Analogues of the growth factor precursor contemplated herein include, but are not limited to, modification to side chains, incorporating of unnatural amino acids and/or their derivatives during peptide, polypeptide or protein synthesis and the use of crosslinkers and other methods which impose conformational constraints on the proteinaceous molecule or their analogues.

Examples of side chain modifications contemplated by the present invention include modifications of amino groups such as by reductive alkylation by reaction with an aldehyde followed by reduction with $NaBH_4$; amidination with methylacetimidate; acylation with acetic anhydride; carbamoylation of amino groups with cyanate; trinitrobenzylation of amino groups with 2, 4, 6-trinitrobenzene sulphonic acid (TNBS); acylation of amino groups with succinic anhydride and tetrahydrophthalic anhydride; and pyridoxylation of lysine with pyridoxal-5-phosphate followed by reduction with $NaBH_4$.

The guanidine group of arginine residues may be modified by the formation of heterocyclic condensation products with reagents such as 2,3-butanedione, phenylglyoxal and glyoxal.

The carboxyl group may be modified by carbodiimide activation via O-acylisourea formation followed by subsequent derivitisation, for example, to a corresponding amide.

Sulphydryl groups may be modified by methods such as carboxymethylation with iodoacetic acid or iodoacetamide; performic acid oxidation to cysteic acid; formation of a mixed disulphides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri-4-nitrophenol and other mercurials; carbamoylation with cyanate at alkaline pH.

Tryptophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form a 3-nitrotyrosine derivative.

Modification of the imidazole ring of a histidine residue may be accomplished by alkylation with iodoacetic acid derivatives or N-carbethoxylation with diethylpyrocarbonate.

Examples of incorporating unnatural amino acids and derivatives during peptide synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids. A list of unnatural amino acid, contemplated herein is shown in Table 1.

Crosslinkers can be used, for example, to stabilise 3D conformations, using homo-bifunctional crosslinkers such as the bifunctional imido esters having $(CH_2)_n$ spacer groups with n=1 to n=6, glutaraldehyde, N-hydroxysuccinimide esters and hetero-bifunctional reagents which usually contain an amino-reactive moiety such as N-hydroxysuccinimide and another group specific-reactive moiety such as maleimido or dithio moiety (SH) or carbodiimide (COOH). In addition, peptides can be conformationally constrained by, for example, incorporation of $C_\alpha$ and $N_\alpha$-methylamino acids, introduction of double bonds between $C_\alpha$ and $C_\beta$ atoms of amino acids and the formation of cyclic peptides or analogues by introducing covalent bonds such as forming an amide bond between the N and C termini, between two side chains or between a side chain and the N or C terminus.

The present invention further contemplates chemical analogues of the growth factor and/or its precursor capable of acting as antagonists or agonists of same. These may be useful in controlling the immunological response. Chemical analogues may not necessarily be derived from the growth factor precursor but may share certain conformational similarities. Alternatively, chemical analogues may be specifically designed to mimic certain physiochemical properties of the growth factor precursor. Chemical analogues may be chemically synthesised or may be detected following, for example, natural product screening of, for example, coral, soil, plants, microorganisms, marine invertebrates or seabeds.

TABLE 1

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane- | Cpro | L-N-methylasparagine | Nmasn |
| carboxylate | | L-N-methylaspartic acid | Nmasp |
| aminoisobutyric acid | Aib | L-N-methylcysteine | Nmcys |
| aminonorbornyl- | Norb | L-N-methylglutamine | Nmgin |
| carboxylate | | L-N-methylglutamic acid | Nmglu |
| cyclohexylalanine | | Chexa L-N-methylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmet |
| D-cysteine | Dcys | L-N-methylnorleucine | Nmnle |
| D-glutamine | Dgln | L-N-methylnorvaline | Nmnva |
| D-giutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |

TABLE 1-continued

| Non-conventional amino acid | Code | Non-conventional amino acid | Code |
|---|---|---|---|
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-methylcyclohexylaianine | Mchexa |
| D-α-methylarginine | Dmarg | α-methylcylcopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylaianine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cylcododecylglycine | Ncdod |
| D-N-methylalanine | Dnmala | N-cyclooctylglycine | Ncoct |
| D-N-methylarginine | Dnmarg | N-cyclopropylglycine | Ncpro |
| D-N-methylasparagine | Dnmasn | N-cycloundecylglycine | Ncund |
| D-N-methylaspartate | Dnmasp | N-(2,2-diphenylethyl)glycine | Nbhm |
| D-N-methylcysteine | Dnmcys | N-(3,3-diphenylpropyl)glycine | Nbhe |
| D-N-methylglutamine | Dnmgln | N-(3-guaniduiopropyl)glycine | Narg |
| D-N-methylglutamate | Dnmglu | N-(1-hydroxyethyl)glycine | Nthr |
| D-N-methylhistidine | Dnmhis | N-(hydroxyethyl))glycine | Nser |
| D-N-methylisoleucine | Dnmile | N-(imidazolylethyl))glycine | Nhis |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthyialanine | Nmanap |
| D-N-methylvaiine | Dnmval | N-methylpenicillamine | Nmpen |
| γ-aminobutyric acid | Gabu | N-(1-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagiine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylomithine | Morn |
| L-α-methylphenylalanie | Mphe | L-α-methylproline | Mpro |
| L-α-methylserie | Mser | L-α-methylthreonine | Mthr |
| L-α-methyltryptophan | Mtrp | L-α-methyltyrosine | Mtyr |
| L-α-methylvaline | Mvai | L-N-methylhomophenylalanine | Nmhphe |
| N-(N-(2,2-diphenylethyl) carbamylmethyl)glycine | Nnbhm | N-(N-(3,3-(diphenylpropyl) carbamylmethyl)glycine 1-carboxy-1-(2,2-diphenyl-ethylamino)cyclopropane | Nnbhe Nmbc |

Other derivatives contemplated by the present invention include a range of glycosylation variants from a completely unglycosylated molecule to a modified glycosylated molecule. Altered glycosylation patterns may result from expression of recombinant molecules in different host cells.

The growth factor and growth factor precursor of the present invention may be produced by recombinant DNA means or by chemical synthetic processes. With respect to the former this aspect of the present invention provides a nucleic acid molecule comprising a sequence of nucleotides encoding a B cell immunoglobulin binding peptide or polypeptide and a T cell epitope.

Generally, the nucleic acid molecule encodes a fusion molecule comprising a B cell immunoglobulin binding peptide or polypeptide and a T cell epitope. In this regard, the nucleic acid molecule would generally comprise a promoter region with the B cell immunoglobulin binding peptide or polypeptide encoding portion operably linked thereto and the T cell epitope portion operably linked to the 3' end thereof. Expression of the nucleic acid molecule of the present invention leads to synthesis of a fusion molecule. In a preferred embodiment the nucleic acid molecule further encodes an antigenic portion and optionally an immunoglobulin portion such as a variable kappa light chain. In some circumstances, purification of one or more recombinant components results in all or a portion of the signal peptide for the ompA or other carrier molecule for the microbial host in which the recombinant molecule is made. This may facilitate multimerisation. In a particularly preferred embodiment of the present invention, the nucleic acid molecule comprises the nucleotide sequence set forth in SEQ ID NO:1 or SEQ ID NO:3 or is a sequence capable of hybridizing thereto under low stringency conditions wherein said nucleotide sequence encodes a growth factor precursor as hereinbefore described.

Still a further aspect of the present invention extends to a method for producing catalytic antibodies to a specific antigen, said method comprising administering to an animal an effective amount of a growth factor precursor comprising an antigen capable of interacting with a B cell bound catalytic antibody said antigen linked to or otherwise associate with a B cell surface molecule binding portion and a portion capable of providing T cell dependent help to a B cell. The growth factor precursor may also comprise a B cell surface molecule binding portion masking entity such as a variable kappa light chain linked to the antigen.

Alternatively, the growth factor precursor may comprise a B cell surface molecule binding portion in multimeric form linked to an antigen for which a target antibody is sought. The portion providing T cell dependent help is preferably a T cell epitope and is preferably part of the precursor. However, it may be a separate entity administered simultaneously or sequentially to an animal.

The present invention also provides catalytic antibodies produced by the above method. The catalytic antibodies are in effect specific to or directed against A of the above formulae. Such catalytic antibodies, therefore, may be directed to any antigen such as but not limited to a cytokine such as but not limited to tumor necrosis factor (TNF), an interleukin (IL) such as IL-1 to IL-15, interferons (IFN) such as IFNα, IFNβ or IFNγ, colony-stimulating factors (CSF) such as granulocyte colony-stimulating factor (G-CSF), ganulocyte-macrophase colony-stimulation factor (GM-CSF), blood factors such as Factor VIII, erythropoietin and haemopoietin, cancer antigens, docking receptors from pathogenic viruses such as HIV, influenza virus or a hepatitis virus (eg. HEP A, HEP B, HEP C or HEP E) and amyloid plaques such as in Alzheimer's disease patients or myeloma patients.

The catalytic antibodies of the present invention have particular therapeutic and diagnostic uses especially in relation to mammalian and more particularly human disease conditions.

Accordingly, the present invention contemplates a pharmaceutical composition comprising a growth factor precursor or a derivative thereof and optionally a modulator of growth factor precursor activity and one or more pharmaceutically acceptable carriers and/or diluents. More particularly, the pharmaceutical composition comprises catalytic antibodies generated by the growth factor precursor of the present invention. These components are hereinafter referred to as the "active ingredients".

The pharmaceutical forms suitable for injectable use include sterile aqueous solutions (where water soluble) or dispersions and sterile powders for the extemporaneous preparation of sterile injectable solutions or dispersion or may be in the form of a cream or other form suitable for topical application. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol and liquid polyethylene glycol, and the like), suitable mixtures thereof, and vegetable oils. The proper fluidity can be maintained, for example, by the use of a coating such as licithin, by the maintenance of the required particle size in the case of dispersion and by the use of superfactants. The preventions of the action of microorganisms can be brought about by various antibacterial and antingal agents, for example, parabens, chlorobutanol, phenol, sorbic acid, thirmerosal and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

When the active ingredients are suitably protected they may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations may, of course, be varied and may conveniently be between about 5 to about 80% of the weight of the unit. The amount of active compound in such therapeutically useful compositions in such that a suitable dosage will be obtained. Preferred compositions or preparations according to the present invention are prepared so that an oral dosage unit form contains between about 0.1 ng and 2000 mg of active compound, preferably between about 0.1 μg and 1500 mg and more preferably between about 1 μg and 100 mg.

The tablets, troches, pills, capsules and the like may also contain the components as listed hereafter: a binder such as gum, acacia, corn starch or gelatin; excipients such as dicalcium phosphate; a disintegrating agent such as corn starch, potato starch, alginic acid and the like; a lubricant such as magnesium stearate; and a sweetening agent such a sucrose, lactose or saccharin may be added or a flavouring agent such as peppermint, oil of wintergreen, or cherry flavouring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavouring such as cherry, orange or mango. Of course, any material used in preparing any dosage unit form should be pharmaceutically purer substantially non-toxic in the amounts employed. In addition, the active compound(s) may be incorporated into sustained-release preparations and formulations.

The present invention also extends to forms suitable for topical application such as creams, lotions and gels.

Pharmaceutically acceptable carriers and/or diluents include any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated. Supplementary active ingredients can also be incorporated into the compositions. These may include immune potentiating molecules, multimer facilitating molecules and pharmaceutically active molecules chosen on the disease conditions being treated.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically acceptable carrier in dosage unit form as hereinbefore disclosed. A unit dosage form can, for example, contain the principal active compound in amounts ranging from 0.1 ng to about 200 mg, more preferably ranging from 0.1 $\mu$g and 1500 mg and even more preferably ranging between 1 $\mu$g and 1000 mg. Expressed in proportions the active compound is generally present in from about 0.5 $\mu$g to about 2000 mg/ml of carrier. In the case of compositions containing supplementary active ingredients, the dosages are determined by reference to the usual dose and manner of administration of the said ingredients.

Still another aspect of the present invention is directed to antibodies to the growth factor precursor and its derivatives. Such antibodies may be monoclonal or polyclonal and are independent to the catalytic antibodies selected by the precursor. The (non-catalytic) antibodies to recombinant or synthetic the growth factor precursor or its derivatives of the present invention may be useful as therapeutic agents but are particularly useful as diagnostic agents. Antibodies may also be generated to the catalytic antibodies generated by the growth factor precursors. All these antibodies have particular application in diagnostic assays for the growth factor or catalytic antibody inducer thereof.

For example, specific antibodies can be used to screen for catalytic antibodies. The latter would be important, for example, as a means for screening for levels of these antibodies in a biological fluid or for purifying the catalytic antibodies. Techniques for the assays contemplated herein are known in the art and include, for example, sandwich assays and ELISA.

It is within the scope of this invention to include any second antibodies (monoclonal, polyclonal or fragments of antibodies or synthetic antibodies) directed to the antibodies discussed above. Both the first and second antibodies may be used in detection assays or a fist antibody may be used with a commercially available anti-immunoglobulin antibody.

Both polyclonal and monoclonal antibodies are obtainable by immunization with the enzyme or protein and either type is utilizable for immunoassays. The methods of obtaining both types of sera are well known in the art. Polyclonal sera are less preferred but are relatively easily prepared by injection of a suitable laboratory animal with an effective amount of antigen, or antigenic parts thereof, collecting serum from the animal, and isolating specific sera by any of the known immunoadsorbent techniques. Although antibodies produced by this method are utilizable in virtually any type of immunoassay, they are generally less favoured because of the potential heterogeneity of the product.

The use of monoclonal antibodies in an immunoassay is particularly preferred because of the ability to produce them in large quantities and the homogeneity of the product. The preparation of hybridoma cell lines for monoclonal antibody production derived by fusing an immortal cell line and lymphocytes sensitized against the immunogenic preparation can be done by techniques which are well known to those who are skilled in the art.

Another aspect of the present invention contemplates a method for detecting an antigen in a biological sample from a subject said method comprising contacting said biological sample with an antibody specific, for said antigen or its derivatives or homologues for a time and under conditions sufficient for an antibody-antigen complex to form, and then detecting said complex. In this context the "antigen" may be a growth factor, its precursor, a component thereof or a catalytic antibody induced thereby.

The presence of antigen may be accomplished in a number of ways such as by Western blotting and ELISA procedures. A wide range of immunoassay techniques are available as can be seen by reference to U.S. Pat. Nos. 4,016,043, 4,424,279 and 4,018,653. These, of course, includes both single-site and two-site or "sandwich" assays of the non-competitive types, as well as in the traditional competitive binding assays. These assays also include direct binding of a labelled antibody to a target.

Sandwich assays are among the most useful and commonly used assays and are favoured for use in the present invention. A number of variations of the sandwich assay technique exist, and all are intended to be encompassed by the present invention. Briefly, in a typical forward assay, an unlabelled antibody is immobilized on a solid substrate and the sample to be tested brought into contact with the bound molecule. After a suitable period of incubation, for a period of time sufficient to allow formation of an antibody-antigen complex, a second antibody specific to the antigen, labelled with a reporter molecule capable of producing a detectable signal is then added and incubated, allowing time sufficient for the formation of another complex of antibody-antigen-labelled antibody. Any unreacted material is washed away, and the presence of the antigen is determined by observation of a signal produced by the reporter molecule. The results may either be qualitative, by simple observation of the visible signal, or may be quantitated by comparing with a control sample containing known amounts of hapten. Variations on the forward assay include a simultaneous assay, in which both sample and labelled antibody are added simultaneously to the bound antibody. These techniques are well known to those skilled in the art, including any minor variations as will be readily apparent In accordance with the present invention the sample is one which might contain an antigen including cell extract, supernatant fluid, tissue biopsy or possibly serum, saliva, mucosal secretions, lymph, tissue fluid and respiratory fluid. The sample is, therefore, generally a biological sample comprising biological fluid but also extends to fermentation fluid and supernatant fluid such as from a cell culture.

In the typical forward sandwich assay, a first antibody having specificity for the antigen or antigenic parts thereof, is either covalently or passively bound to a solid surface. The solid surface is typically glass or a polymer, the most commonly used polymers being cellulose, polyacrylamide, nylon, polystyrene, polyvinyl chloride or polypropylene. The solid supports may be in the form of tubes, beads, discs of microplates, or any other surface suitable for conducting an immunoassay. The binding processes are well-known in the art and generally consist of cross-lining covalently binding or physically adsorbing, the polymer-antibody complex is washed in preparation for the test sample. An aliquot of the sample to be tested is then added to the solid phase complex and incubated for a period of time sufficient (e.g. 2–40 minutes) and under suitable conditions (e.g. 25° C.) to allow binding of any subunit present in the antibody. Following the incubation period, the antibody subunit solid phase is washed and dried and incubated with a second antibody specific for a portion of the hapten. The second antibody is linked to a reporter molecule which is used to indicate the binding of the second antibody to the hapten.

An alternative method involves immobilizing the target molecules in the biological sample and then exposing the immobilized target to specific antibody which may or may not be labelled with a reporter molecule. Depending on the amount of target and the strength of the reporter molecule signal, a bound target may be detectable by direct labelling with the antibody. Alternatively, a second labelled antibody, specific to the first antibody is exposed to the target-first antibody complex to form a target-first antibody-second antibody tertiary complex. The complex is detected by the signal emitted by the reporter molecule.

By "reporter molecule" as used in the present specification, is meant a molecule which, by its chemical nature, provides an analytically identifiable signal which allows the detection of antigen-bound antibody. Detection may be either qualitative or quantitative. The most commonly used reporter molecules in this type of assay are either enzymes, fluorophores or radionuclide containing molecules (i.e. radioisotopes) and chemiluminescent molecules. In the case of an enzyme immunoassay, an enzyme is conjugated to the second antibody, generally by means of glutaraldehyde or periodate. As will be readily recognized, however, a wide variety of different conjugation techniques exist, which are readily available to the skilled artisan. Commonly used enzymes include horseradish peroxidase, glucose oxidase, beta-galactosidase and alkaline phosphatase, amongst others. The substrates to be used with the specific enzymes are generally chosen for the production, upon hydrolysis by the corresponding enzyme, of a detectable colour change. Examples of suitable enzymes include alkaline phosphatase and peroxidase. It is also possible to employ fluorogenic substrates, which yield a fluorescent product rather than the chromogenic substrates noted above. In all cases, the enzyme-labelled antibody is added to the first antibody hapten complex, allowed to bind, and then the excess reagent is washed away. A solution containing the appropriate substrate is then added to the complex of antibody-antigen-antibody. The substrate will react with the enzyme linked to the second antibody, giving a qualitative visual signal, which may be further quantitated, usually spectrphotometrically, to give an indication of the amount of hapten which was present in the sample. "Reporter molecule" also extends to use of cell agglutination or inhibition of agglutination such as red blood cells on latex beads, and the like.

Alternately, fluorescent compounds, such as fluorescein and rhodamine, may be chemically coupled to antibodies without altering their binding capacity. When activated by illumination with light of a particular wavelength, the fluorochrome-labelled antibody adsorbs the light energy, inducing a state to excitability in the molecule, followed by emission of the light at a characteristic colour visually detectable with a light microscope. As in the EIA, the fluorescent labelled antibody is allowed to bind to the first antibody-hapten complex. After washing off the unbound reagent, the remaining tertiary complex is then exposed to the light of the appropriate wavelength the fluorescence observed indicates the presence of the hapten of interest. Immunofluorescene and EIA techniques are both very well established in the art and are particularly preferred for the present method. However, other reporter molecules, such as radioisotope, chemiluminescent or bioluminescent molecules, may also be employed.

The present invention may use any number of means to clone genetic sequences encoding catalytic antibodies. For example, a phage display library potentially capable of expressing a catalytic antibody on the phage surface may be used to screen for catalysis of defined antigens.

The present invention further contemplates the use of the products of catalysis of a growth factor precursor to induce B cell mitogenesis to generate catalytic antibodies to a specific antigen.

More particularly, the present invention contemplates the use of a growth factor precursor comprising an antigen to which a catalytic antibody is sought linked, fused or otherwise associated to a B cell surface molecule binding portion in the induction of B cell mitogenesis following catalytic cleavage of all or part of said antigen.

Still another embodiment of the present invention contemplates the use of an antigen linked, fused or otherwise associate to a B cell surface molecule binding portion in the manufacture of a growth factor precursor to induce B cell mitosis following catalytic cleavage of all or part of said antigen.

The present invention is further described by the following non-limiting figures and/or examples.

In the figures:

FIG. 1 is a schematic representation of the three overlapping synthetic oligonucleotides used to generate a genetic construct encoding LHL.

FIG. 2 is a photographic representation of LEL in a bacterial lysate after purification on a human IgG (huIgG) affinity column. First lane, uninduced; second lane, induced LHL sample; right lane, purified LHL with size of approximately 18 kDa.

FIG. 3 is a schematic representation of LHL.seq carrying two affinity tags.

FIG. 4 is a photographic representation showing an LHL.seq expression and purification analysed on a 20% w/v polyacrylamide SDS silver stained PHAST-gel.

L=recombinant DH10B lysate after o/n induction of LHL.seq expression; S-streptavidin purified LHL.seq protein; H-huIgG purified LUL.seq protein; e-eluted with 1 mg/ml diaminobiotin, PBS (S) or with 100 mM glycine pH2.0 (H); b-elution of LHL.seq via boiling in loading buffer. Purifications were performed in 1.5 ml eppendorf tubes at RT. 50 µl lysate was incubated with 25 µl column matrix for 15 min. Column material was then washed twice with 500 µl PBS, 0.5% v/v Triton X-100 before eluting with 50 µl solution or boiling as described. Elution of LHL.seq from huIgG matrix is very inefficient in this particular set up although it is the most effective and preferred way when washing on a larger scale affinity column.

Figure 5:
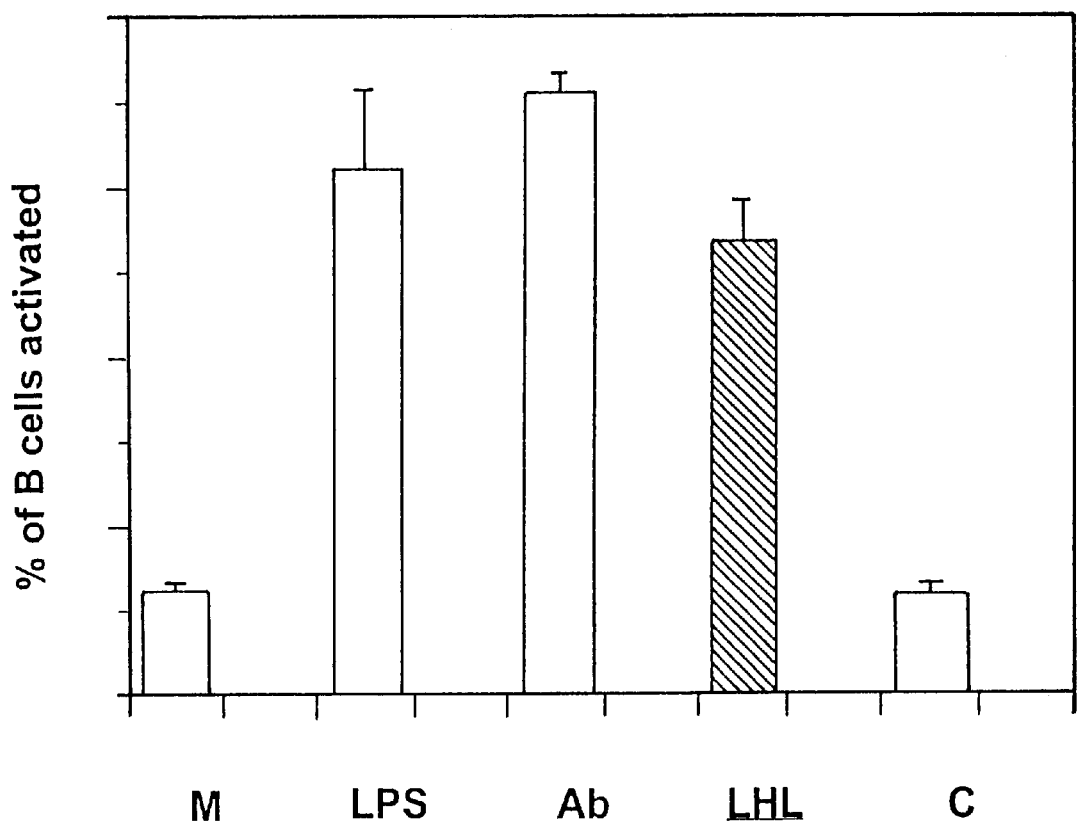

FIG. 5 is a graphical representation showing mitogenic activity of LHL on B cells. M, medium; LPS, lipopolysaccharide; Ab, anti-IgM antibody; C, induced "empty" expression vector and LHL. Y axis (0–100%): percentage of B cells expressing B7.2 after overnight incubation of mesenteric lymphnode cells with substance shown on X axis.

Figure 6:
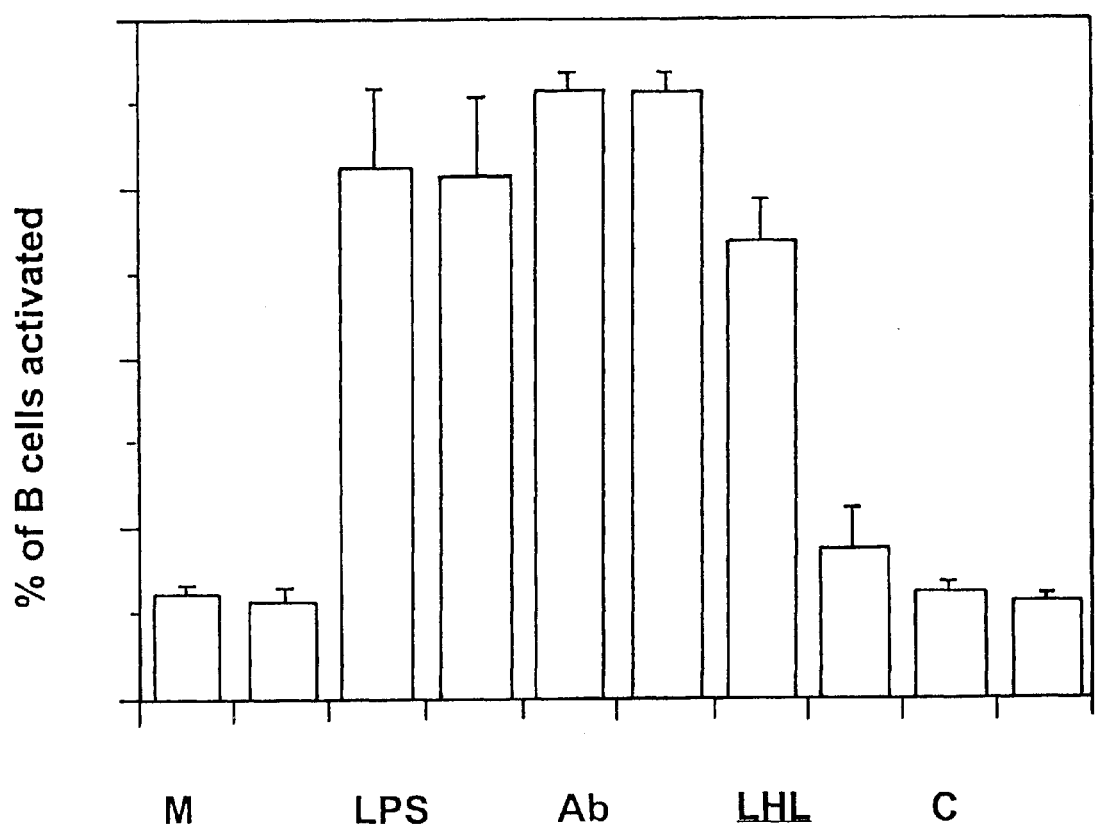

FIG. 6 is a graphical representation as for FIG. 5 with the hatched bars showing the experiment in the presence of human IgG at 500 µg/ml.

Figure 7:
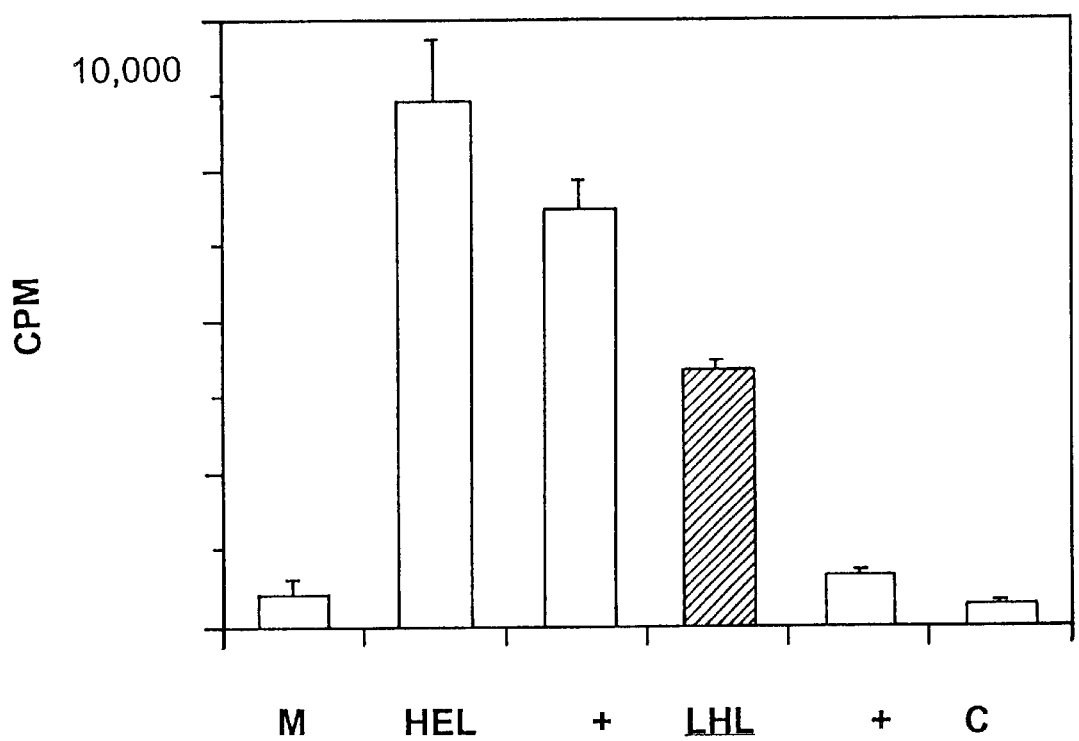

FIG. 7 is a graphical representation showing $^3$H-thymidine incorporation during DNA synthesis (CPM) of the IL-2-dependent CTLL incubated with supernatant of co-cultures as listed below. Splenocytes or mesenteric lymphocytes are co-cultured with T cell hybridoma 3A9 in the presence of M, medium; HEL, hen egg lysozyme; and LHL. The hatched bar for each of HEL and LHL is the same experiment in the presence of human IgG (HuIgG).

Figure 8:
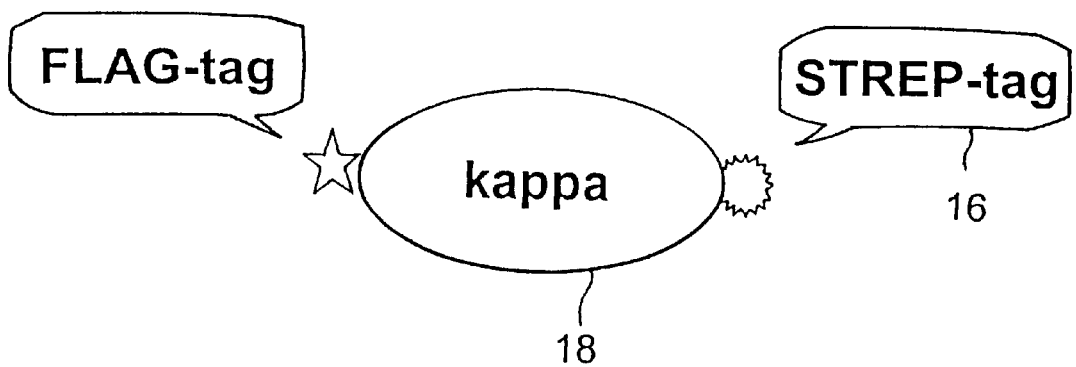

FIG. 8 is a schematic representation of the kappa variable light chain and its two affinity tags.

Figure 9:
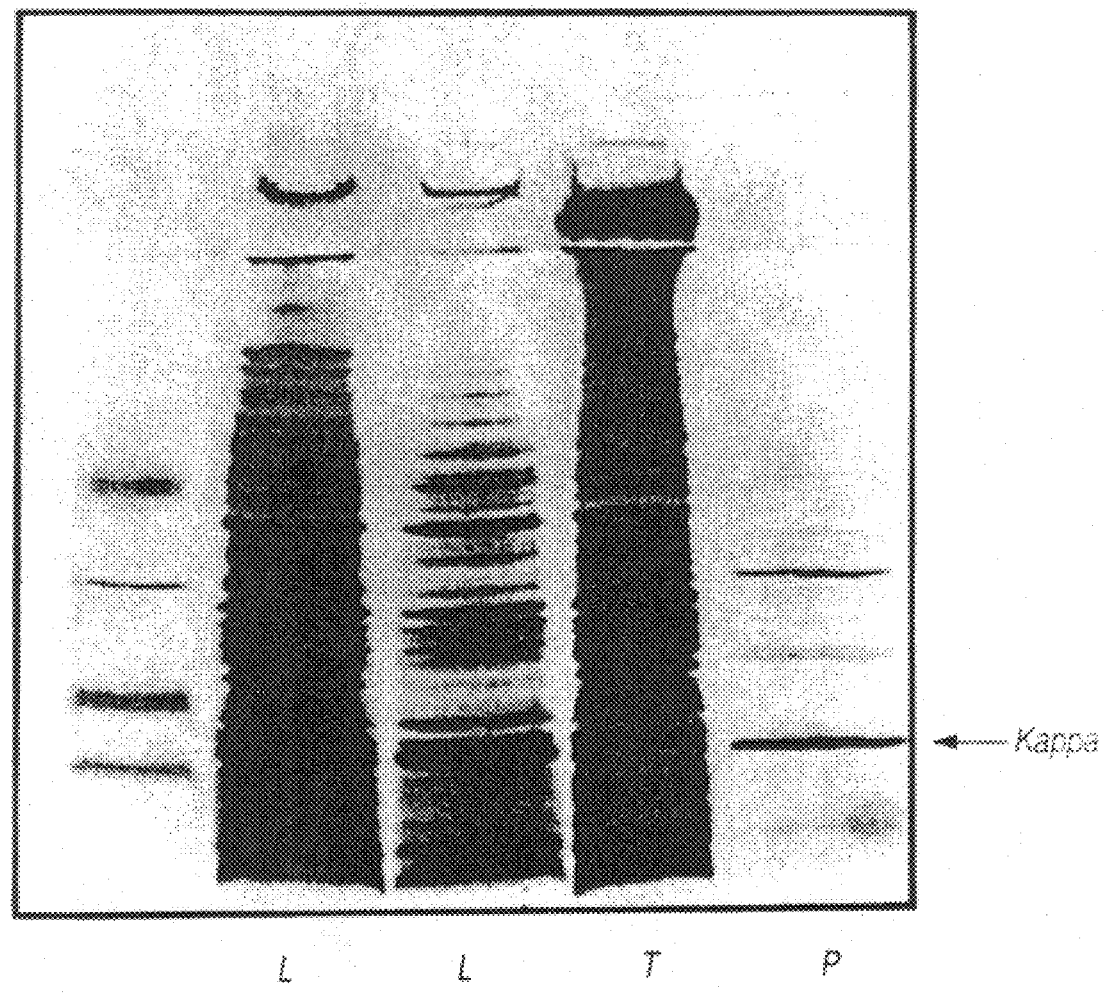

FIG. 9 is a photographic representation showing kappa expression analysed on a 20% w/v polyacrylamide SDS PHAST-gel after silver staining. L=total lysate of two different recombinant DH10B clones induced to express kappa; T=pellet after periplasmic fractionation; P=periplasmic fraction with kappa protein.

Figure 10:
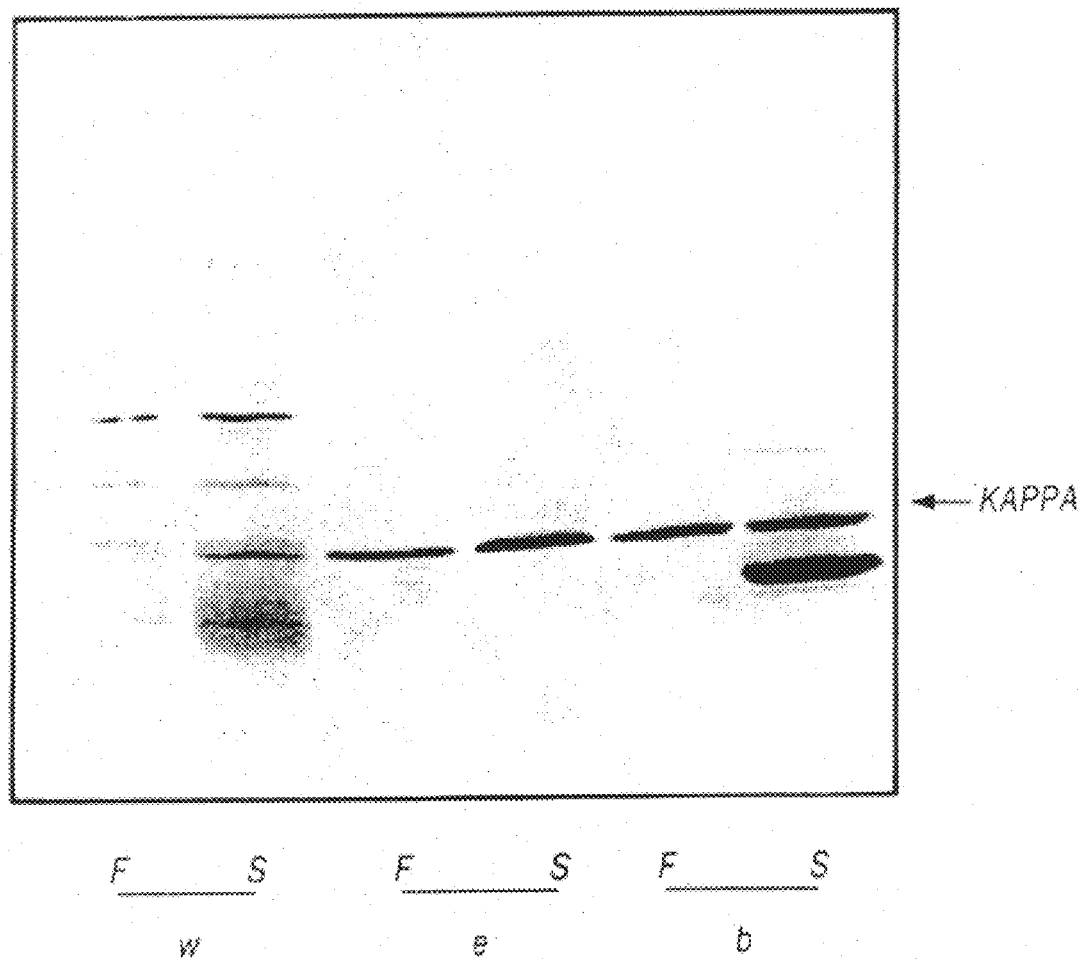

FIG. 10 is a photographic representation showing purified kappa protein on a 20% w/v polyacrylamide SDS PHAST-gel after silver staining. w=periplasmic fraction after incubation with column material; e=eluates using (F) 500 mM EDTA in case of the $Ca^{++}$ dependent anti-Flag affinity column or (S) 50 mM diaminobiotin in case of the streptavidin column; b=eluates from (F) and (S) derived by boiling in loading buffer.

Figure 11:
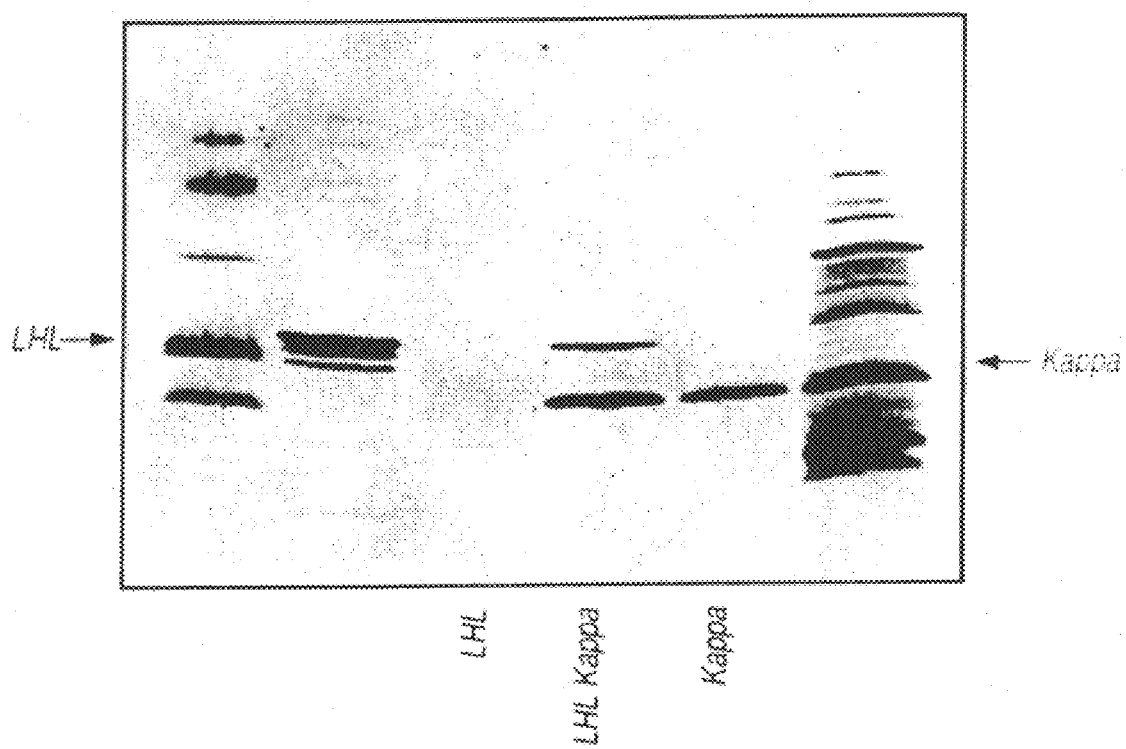

FIG. 11 is a photographic representation of LHL purified via kappa-loaded streptavidin column as shown on a silver stained 20% w/v polyacrylamide SDS PHAST-gel. LHL= LHL alone plus streptavidin matrix; LHL-kappa=LHL purified on the kappa-loaded streptavidin matrix; kappa=kappa alone bound to streptavidin matrix.

Figure 12:
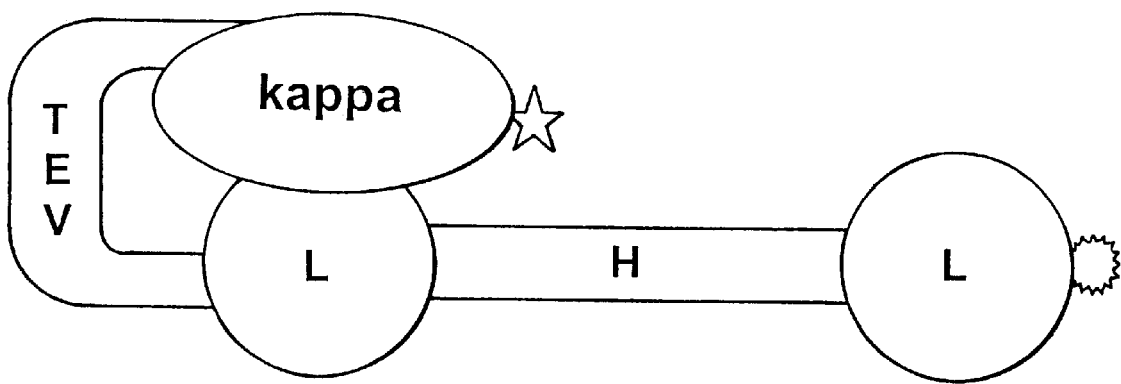

FIG. 12 is a schematic representation of the CATAB pecursor TLHL.

Figure 13:
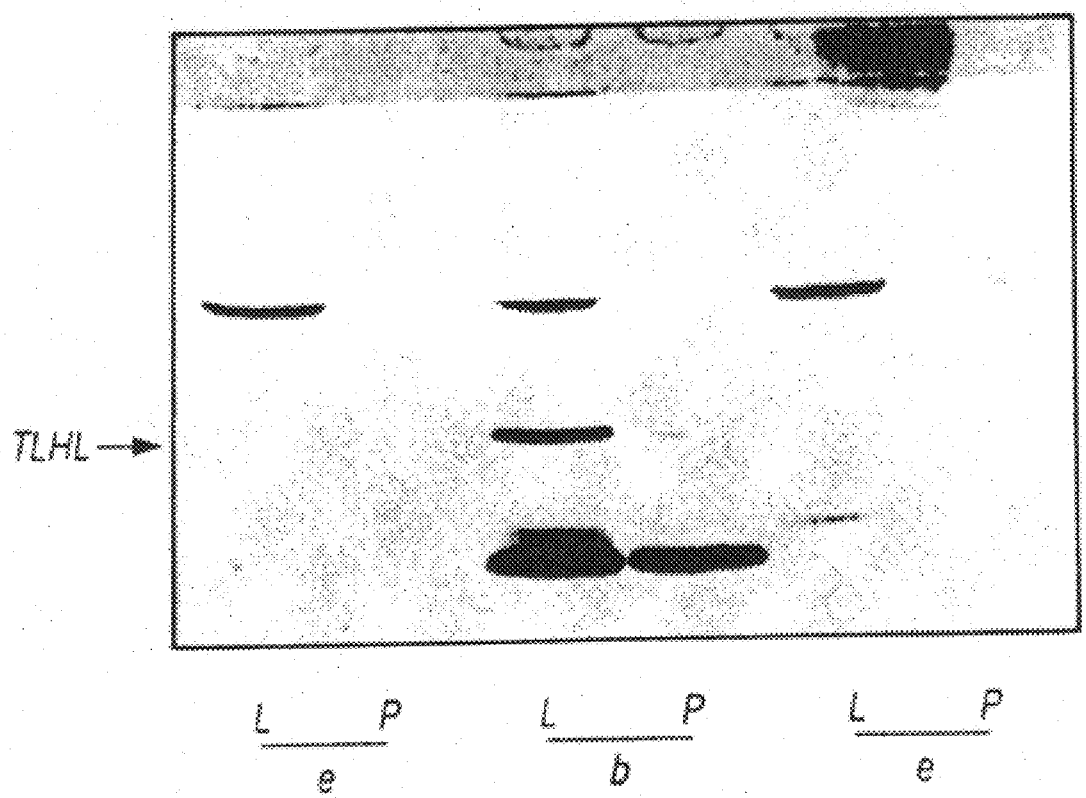

FIG. 13 is a photographic representation of a silver stained 20% w/v polyacrylamide SDS PHAST-gel analysis of purified TLHL from two different recombinant DH10B clones. L=total lysate; P=periplasmic fraction; e=eluted with 50 mM diaminobiotin, b=eluted by boiling in loading buffer.

Figure 14:
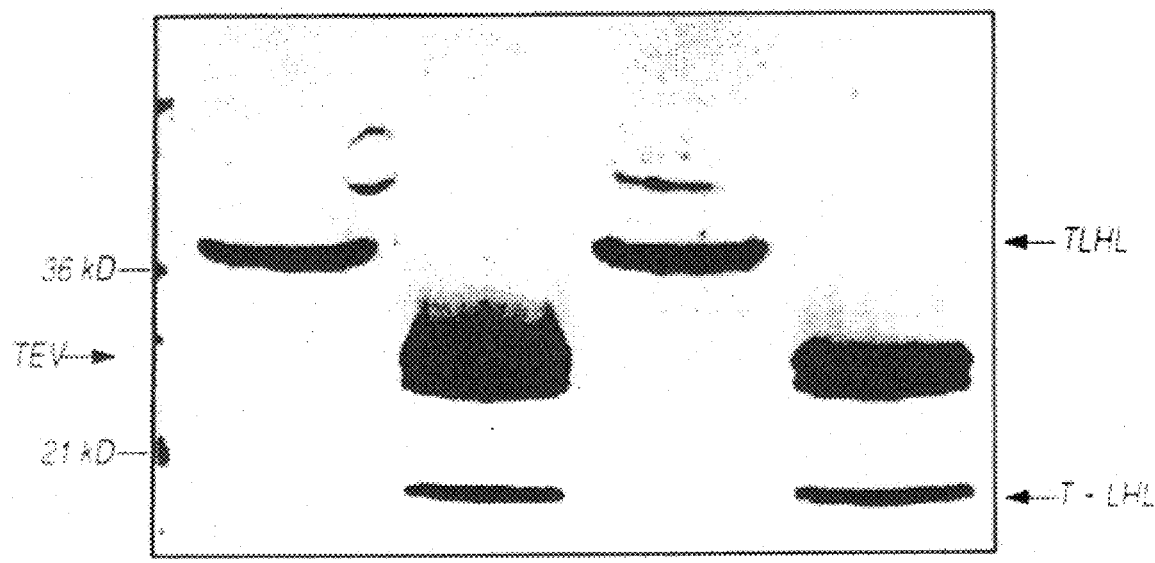

FIG. 14 is a photographic representation of a silver stained 20% w/v polyacrylamide SDS PHAST-gel of TEV cleaved TLHL. Lane one=TLHL uncleaved; lane two= TLHL cleaved with 10 units of TEV; lane three and four= cleavage was performed in 20 µl instead of 10 µl volume as in lane one and two. The identity of the TEV protease band was confirmed in later experiments.

Figure 15:
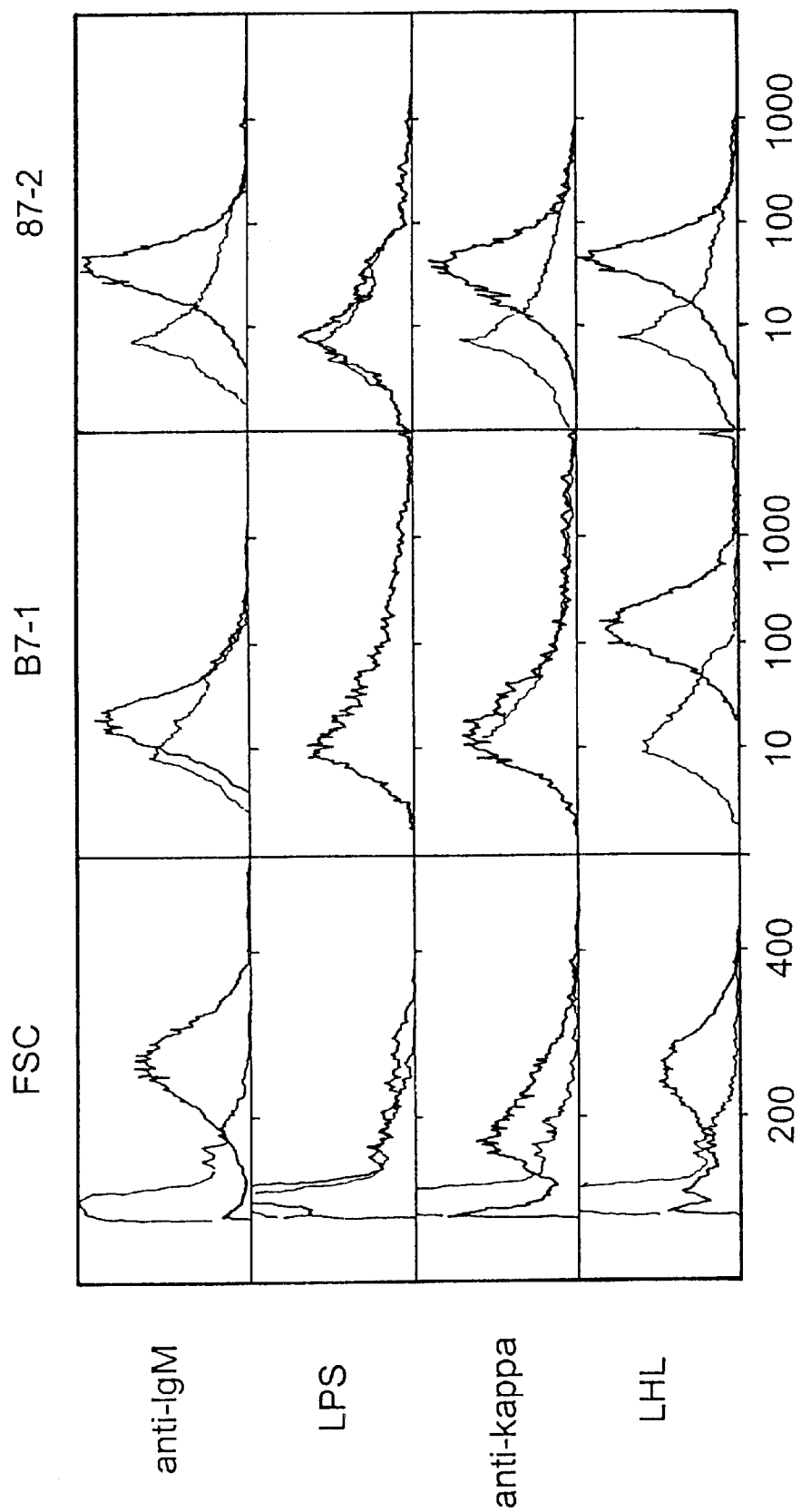

FIG. 15 is a representation showing LHL.seq induced B cell activation: fsc, b7-1, b7-2 analysis by FACS. Mesenteric lymphnode cells from C3H/HeJ were stimulated in triplicate cultures at $3 \times 10^5$/well. Upregulation of activation markers on B cells was monitored by gating on $B220^+Thy1^-$ cells to identify B cells. Results are expressed as FACS-histogramms, showing FSC and B7-1 and B7-2 staining levels. Grey lines indicate background staining from cells incubated in medium alone and black lines show individual results. Anti IgM and anti kappa were included as positive controls and LPS as a negative control.

Figure 16:
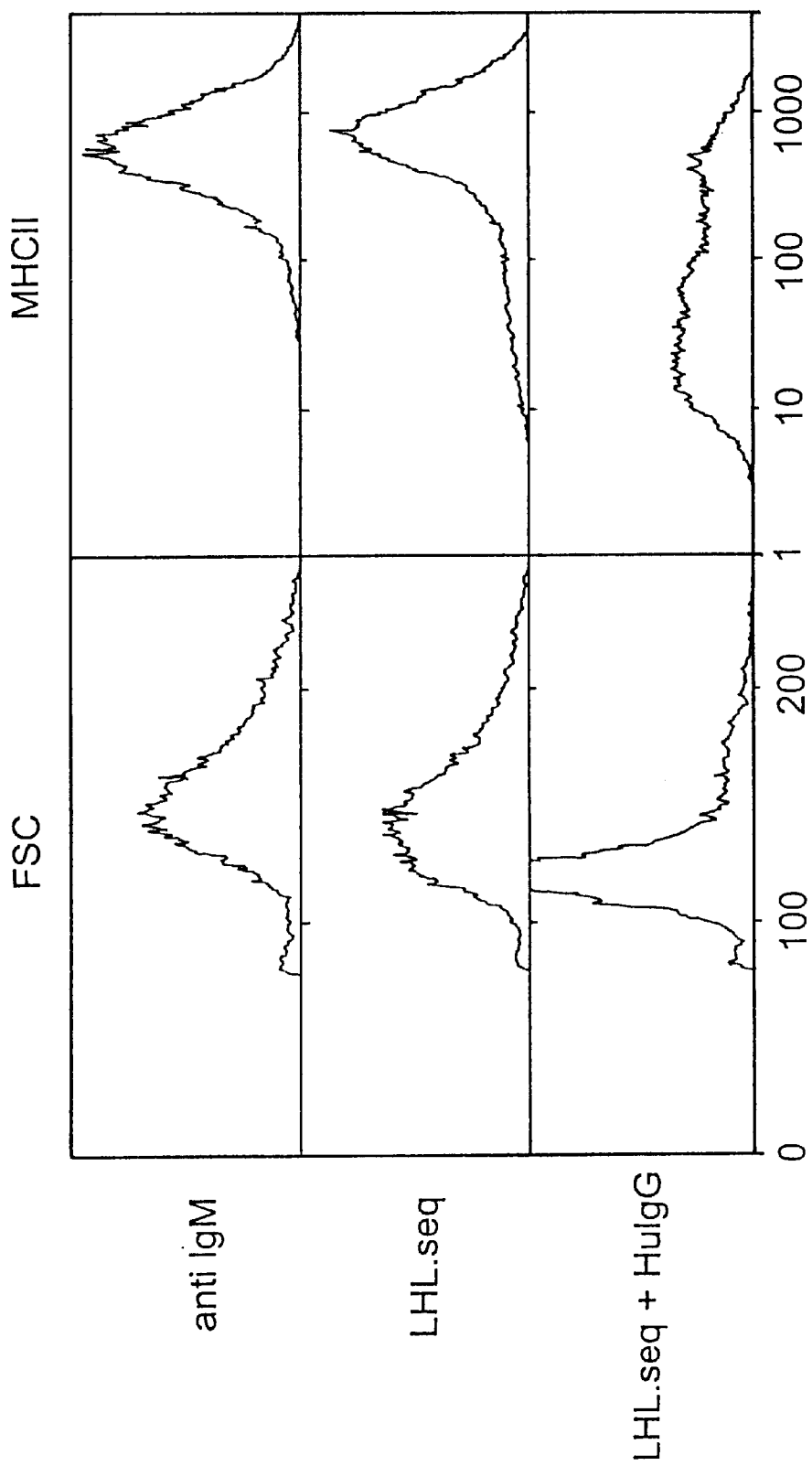

FIG. 16 is a representation showing LHL.seq induced B cell activation: FSC, MHC Class II analysis by FACS. FACS-Analysis was performed as described above. Grey lines indicate background staining from cells incubated in medium alone and black lines show individual results. Anti IgM is positive control and LHL.seq plus huIgG as a control.

Figure 17A:
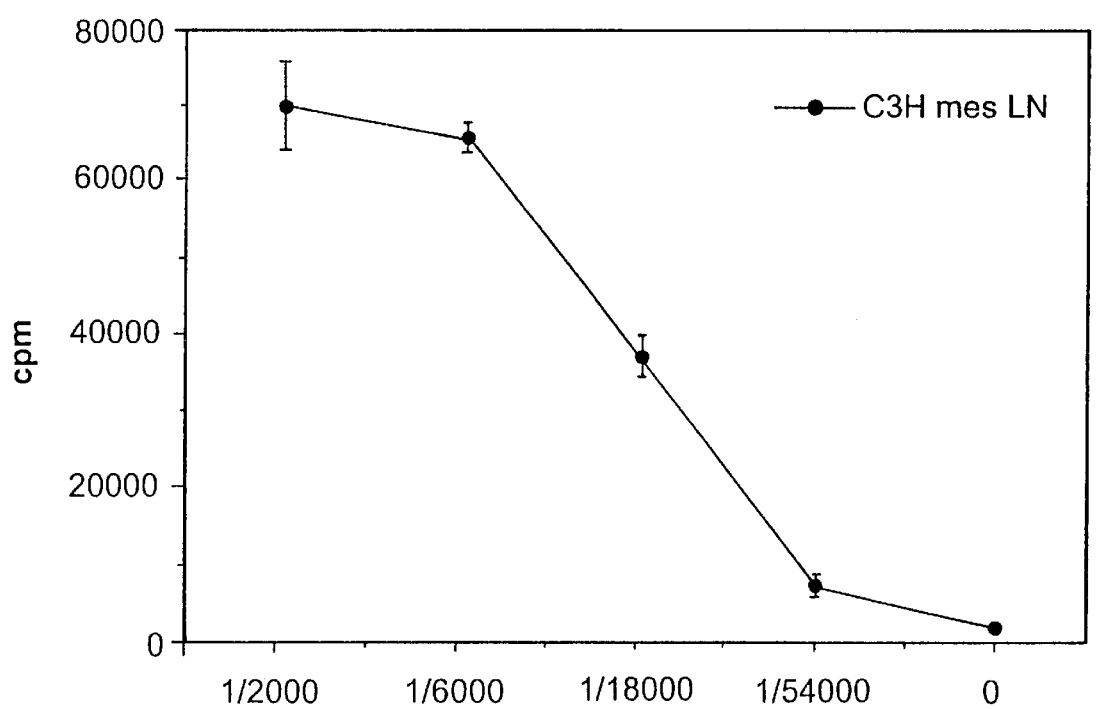
Figure 17B:
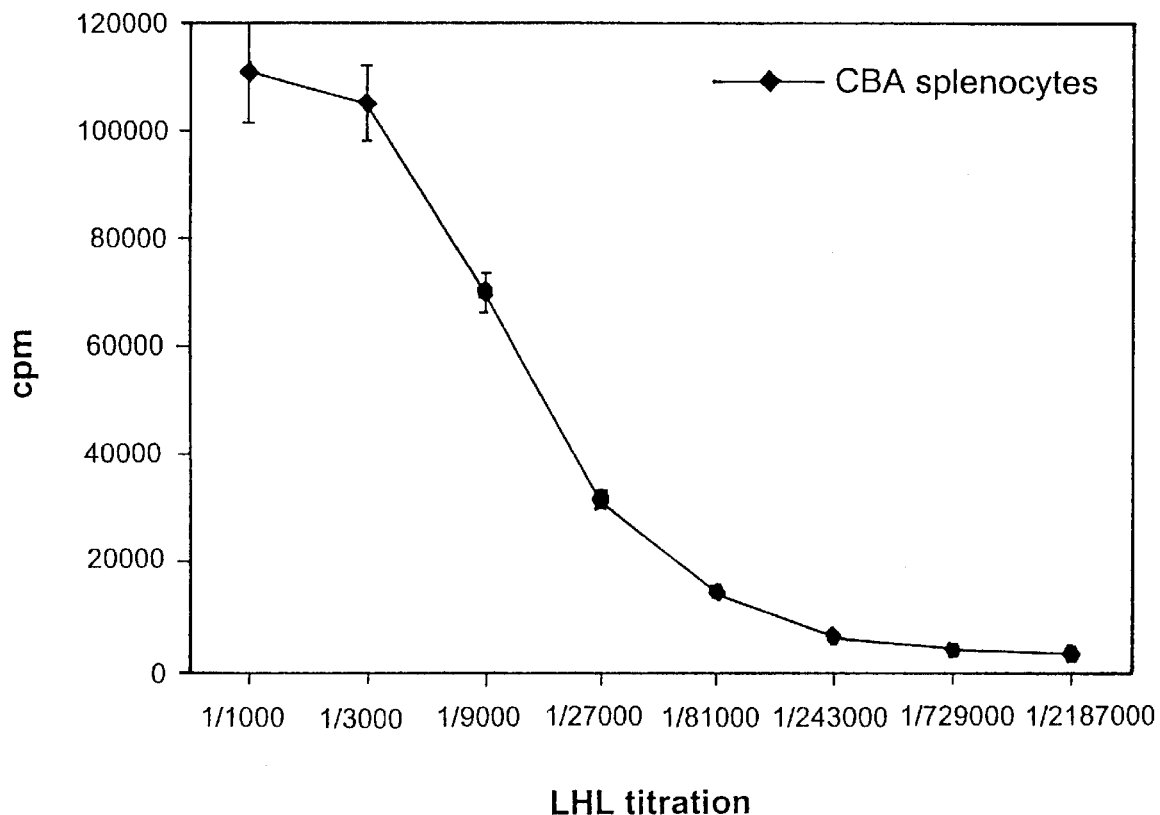

FIG. 17 is a representation showing LHL.seq induced B cell activation: dose-response analysis in proliferation assays. Mesenteric lymphnode cells from C3H/HeJ (upper panel) and splenocytes from CBA/J mice (lower panel) were prepared as described above. The lymphocytes were stimulated in triplicate cultures at $1 \times 10^5$/well in flat bottom 96-well plates in complete RPMI+10% FCS medium at 37° C. for 2 days. Cells are pulsed for the last 6 hours with $^3$H-thymidine. DNA was harvested onto glassfibre filters and incorporation of $^3$H-thymidine was measured in a β-counter. Results are expressed as mean of triplicate cultures including standard deviation.

Figure 18:
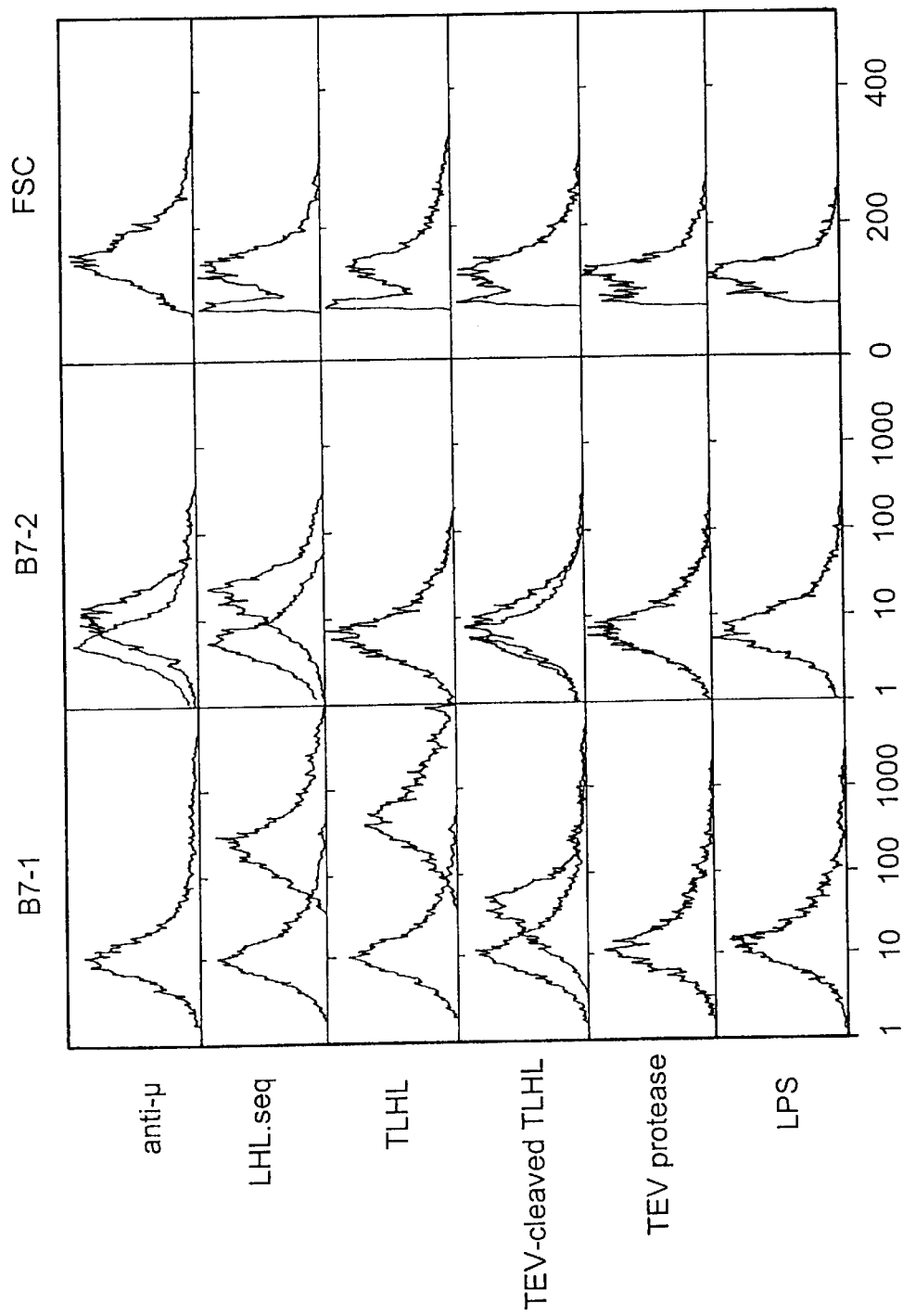

FIG. 18 is a representation showing TLHL induced B cell activation: analysis FACS. Mesenteric lymph node cells from C3H/HeJ mice were centrifuged in Nycodenz (1.091 g/cm$^3$) followed by 1 hour adherence on plastic at 37° C. Lymphocytes were stimulated at $3 \times 10^5$ cells per well with LPS, anti-IgM antibodies, LHL.seq, TLHL and TEV-cleaved TLHL. On day 1 of culture cells were stained for B7-1 and B7-2. B lymphocytes were identified by expression of B220 and lack of expression of Thy 1.2. The activation status of B cells was confirmed by the increase of their FSC and expression of B7-2 and B7-1.

Figure 19:
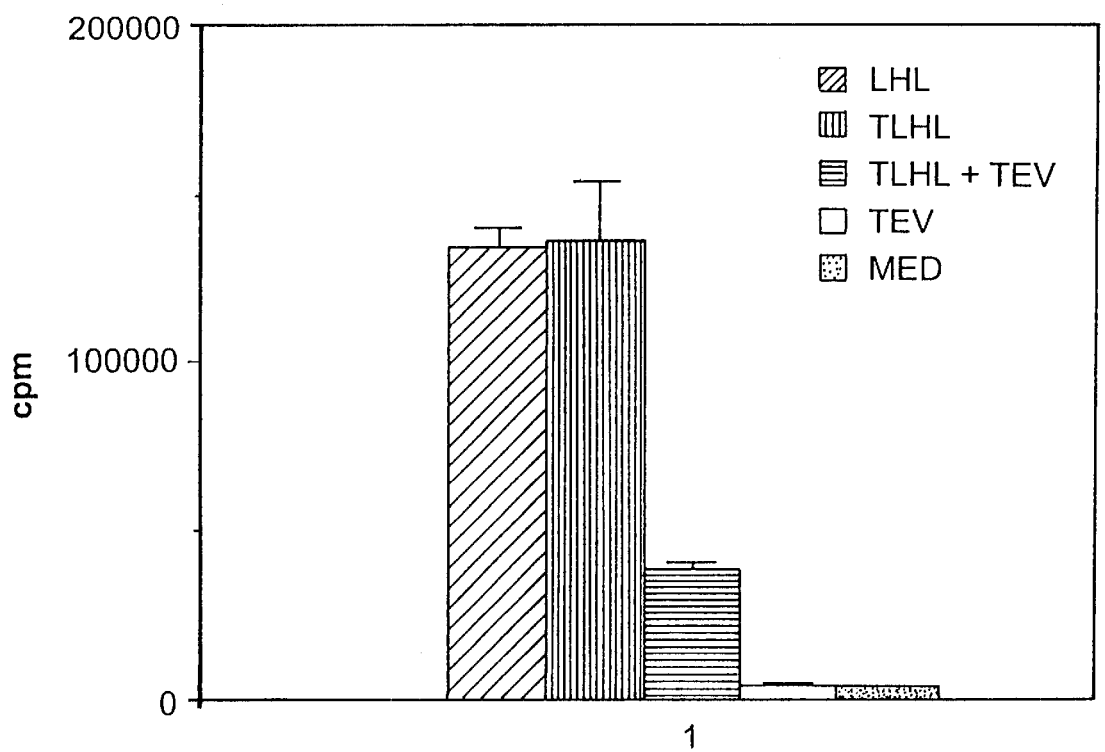

FIG. 19 is a representation showing TLHL induced B cell activation: analysis by proliferation assay $2 \times 10^5$ splenocytes from CBA/J mice were cultured and stimulated as described. On day 2 of culture the cells were pulsed for 6hrs with $^3$H thymidine. The incorporation of $^3$H thymidine is shown in counts per minute (cpm). MED=medium alone; TEV=TEV protease; TLHL=TLHL; TLHL+TEV=TEV-cleaved TLHL; LHL=LHL.seq.

Figure 20:
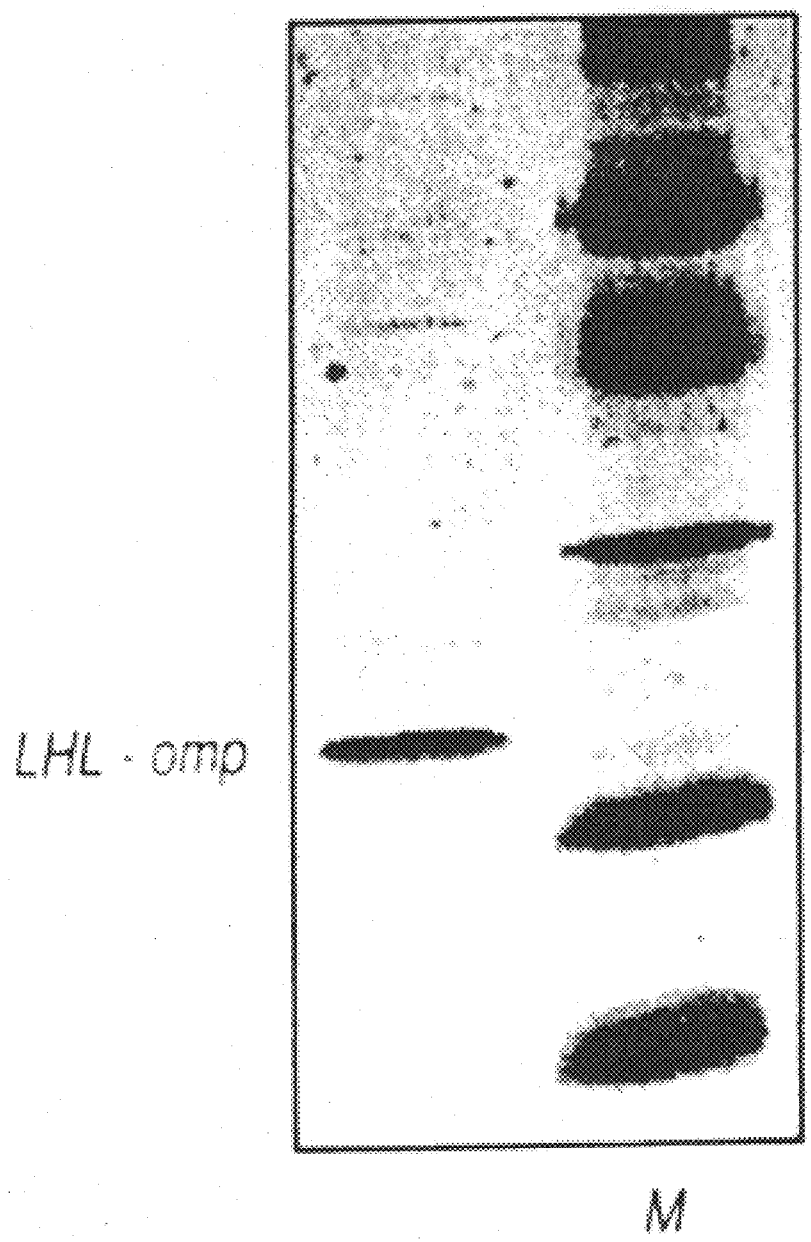

FIG. 20 is a representation showing purification of LHL-OMP on a silver stained 20% w/v polyacrylamide SDS PHAST-gel analysis of huIgG affinity column purified LHL-omp from total DH10B cell lysate. LHL-omp was run next to a molecular size marker and shows the correct molecular weight of approximately 19.5 kD.

Figure 21:
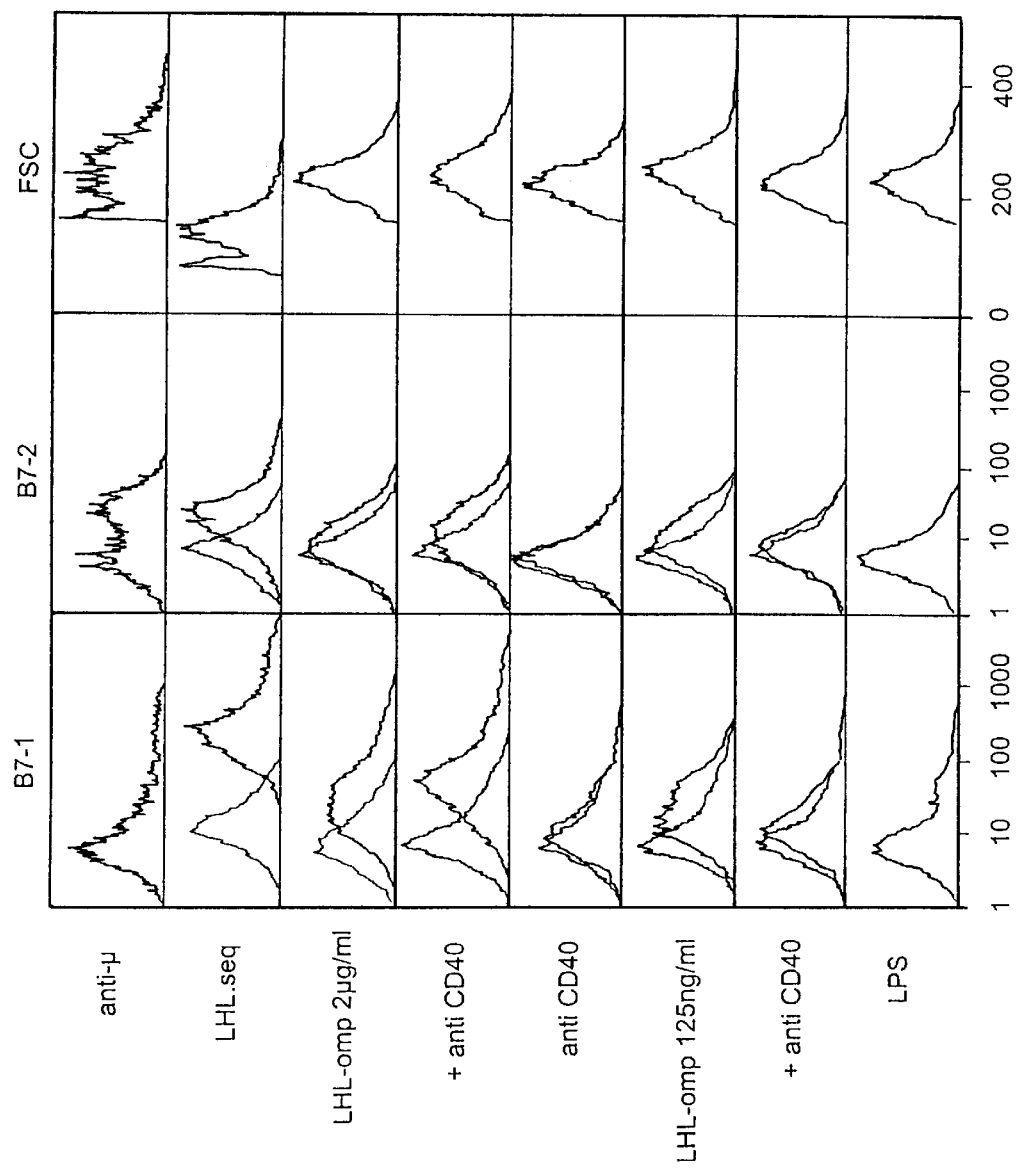

FIG. 21 is a representation showing LHL-OMP induced B cell activation. Splenocytes of C3H/HeJ mice were centriged in Nycodenz (1.091 g/cm$^3$) followed by 1 hour adherence on plastic at 37° C. Cells were stimulated at $3 \times 10^5$ per well with LPS, anti-IgM antibodies, LHL.seq at 1 µg/ml, LHL-omp at 2 µg/ml, anti CD40 mAb (clone FGK45.5) at 0.5 µg/ml, LHL-omp at 125 ng/ml and combinations of both concentrations of LHL-omp with anti-CD40. On day 1 afer stimulation cells were stained for B7-1 and B7-2. B lymphocytes were identified by expression of B220 and lack of expression of Thy 1.2. The activation status of B cells was confirmed by increase of their FSC and by expression of B7-2 and/or B7-1. LHL.seq data taken from representative experiments (for example, FIG. 18).

Figure 22:
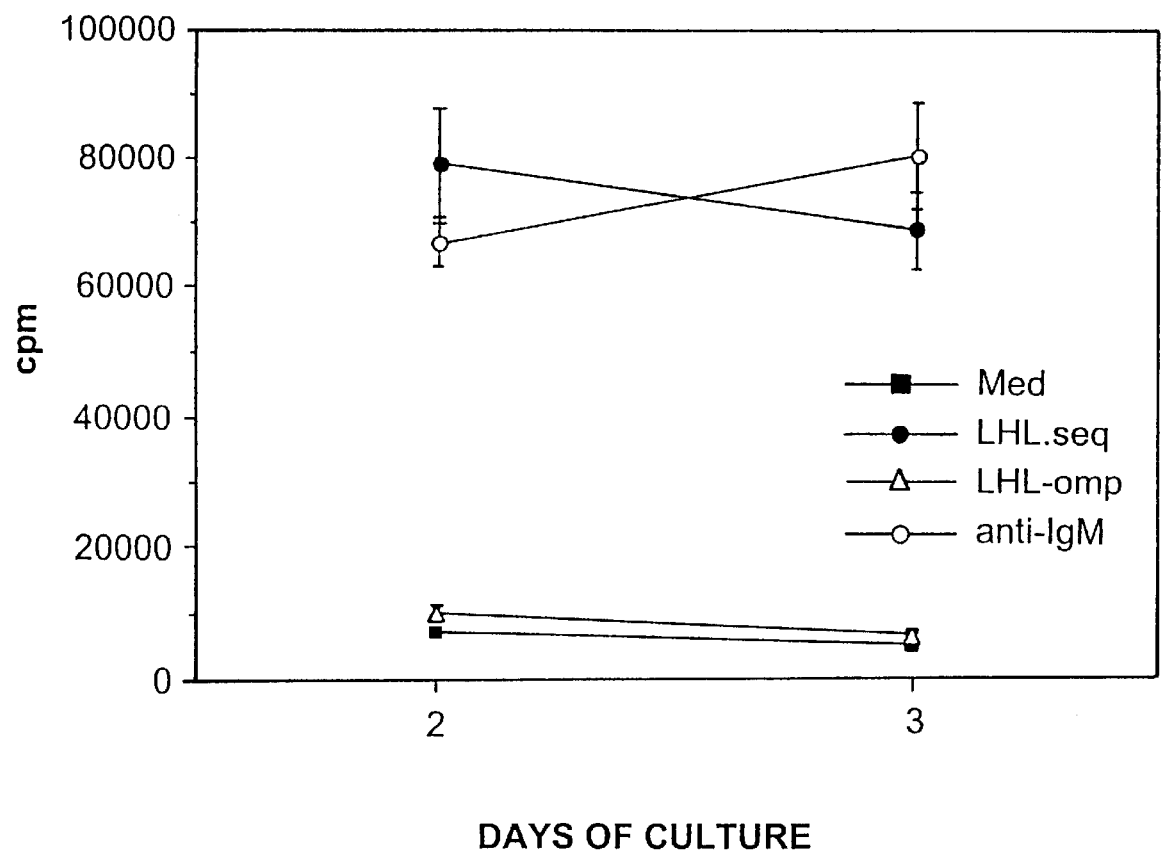

FIG. 22 is a representation showing LHL-OMP induced B cell proliferation. Splenocytes of C3H/HeJ mice were centrifuged in Nycodenz (1.091 g/cm³) followed by 1 hour adherence on plastic at 37° C. Cells were stimulated at 2×10⁵ per well with LHL.seq (1 μg/ml). anti-IgM antibodies (20 μg/ml) and LHL-omp (2 μg/ml). After 2 and 3 days of culture the cells were pulsed with ³H thymidine. ³H thymidine-incorporation into DNA was assessed in a β-counter.

Figure 23:
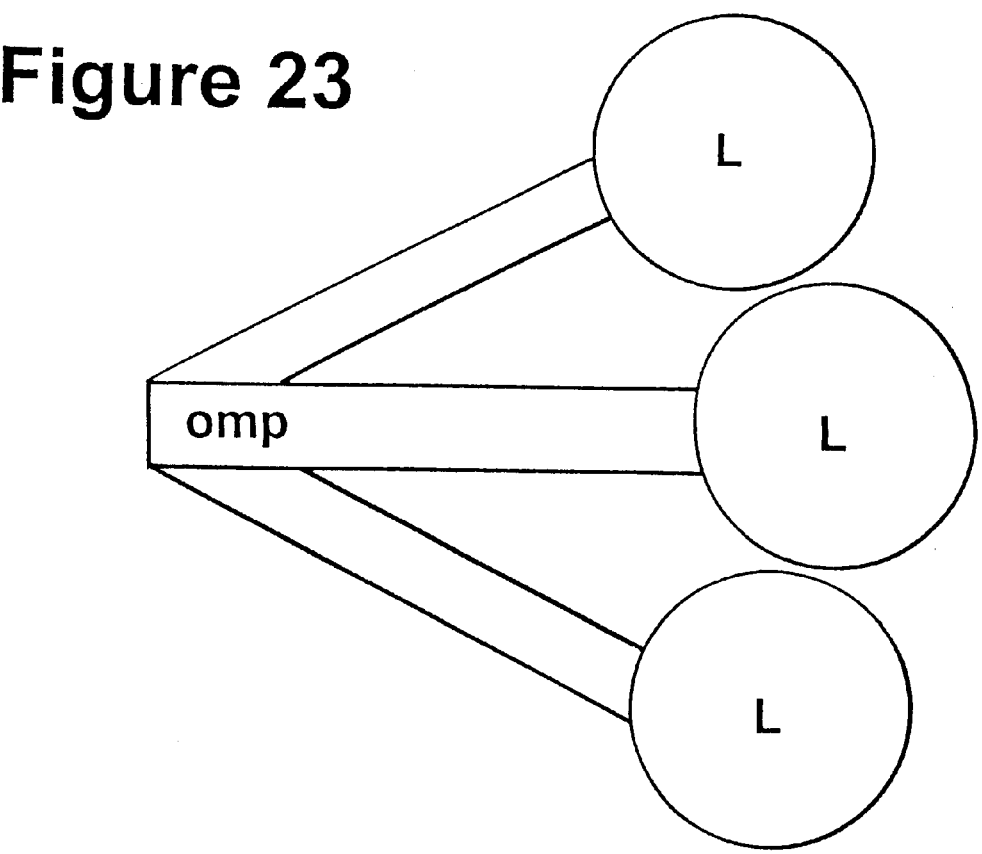
Figure 24:
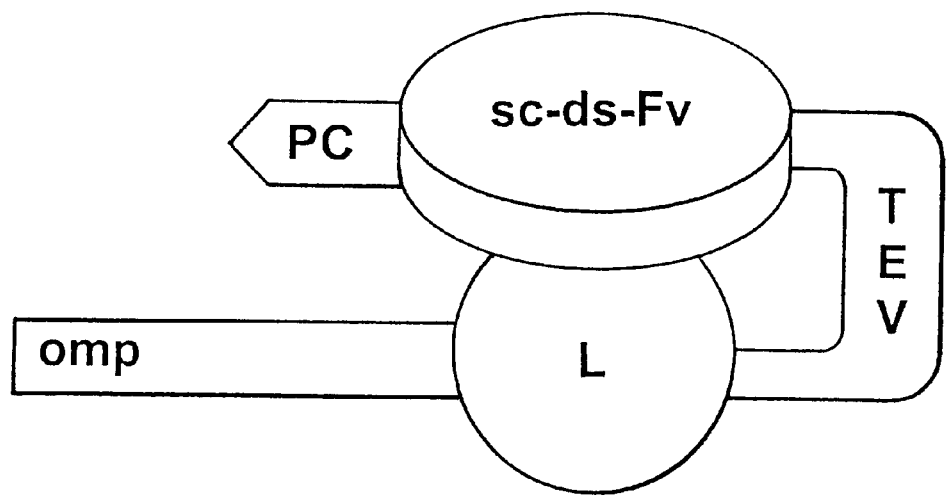

FIG. 23 is a schematic representation of ompL.
FIG. 24 is a schematic representation of Fv-catAb.

SUMMARY OF SEQ ID NOs.

| MOLECULE | SEQ ID NO | |
|---|---|---|
| | Nucleotide | Amino acid |
| LHL | 1 | 2 |
| CATAB-TEV | 3 | 4 |
| TLHL | 5 | 6 |
| LHL.seq | 7 | 8 |
| FLAG epitope | — | 9 |
| Kappa | 10 | 11 |
| LHL-omp | 12 | 13 |
| Strep-tag | — | 14 |

EXAMPLE 1

Generation of LHL from Synthetic Oligonucleotides

LHL was generated from three overlapping synthetic oligos, a 115 mer, a 116 mer and a 105 mer, using the proofreading DNA polymerase Pfu in two 20 cycle PCR reactions (see FIG. 1). The two PCR products (290 bp and 200 bp) were purified and blunt end cloned into the expression vector pASK75. The sequence was verified by automated sequencing. All subsequent PCRs were done in a similar fashion as described in the literature. The nucleotide and corresponding amino acid sequence for LHL is shown in SEQ ID NO:1 and SEQ ID NO:2 respectively.

EXAMPLE 2

Figure 2:

Expression of LHL in *E. coli* and Purification Over a Human IgG (huIgG) Affinity Column The expression vector pASK75 directs protein expression via the ompA signal peptide into the periplasm of *E. coli*. Protein expression was induced with 200 ng/ml anhydrotetracycline for 16 hrs in midlog *E. coli* DH10B cultures. Cells were lysed and soluble LHL purified (>95%) over a huIgG affinity column (FIG. 2). Extensive washes with 0.5% v/v Triton X-100 were performed on the affinity column in order to eliminate endotoxins from the preparations. Expression levels were estimated at 20 mg per liter of culture.

EXAMPLE 3

Figure 3:
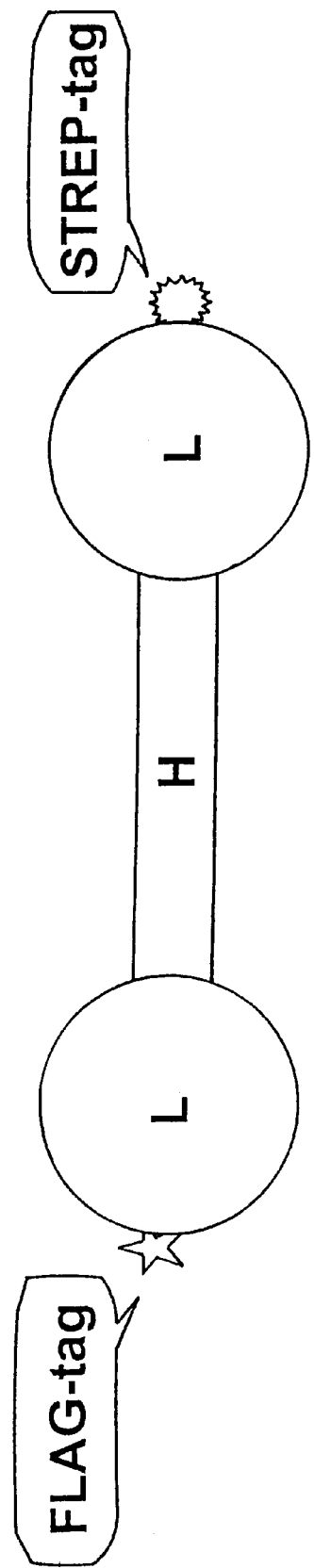
Figure 4:
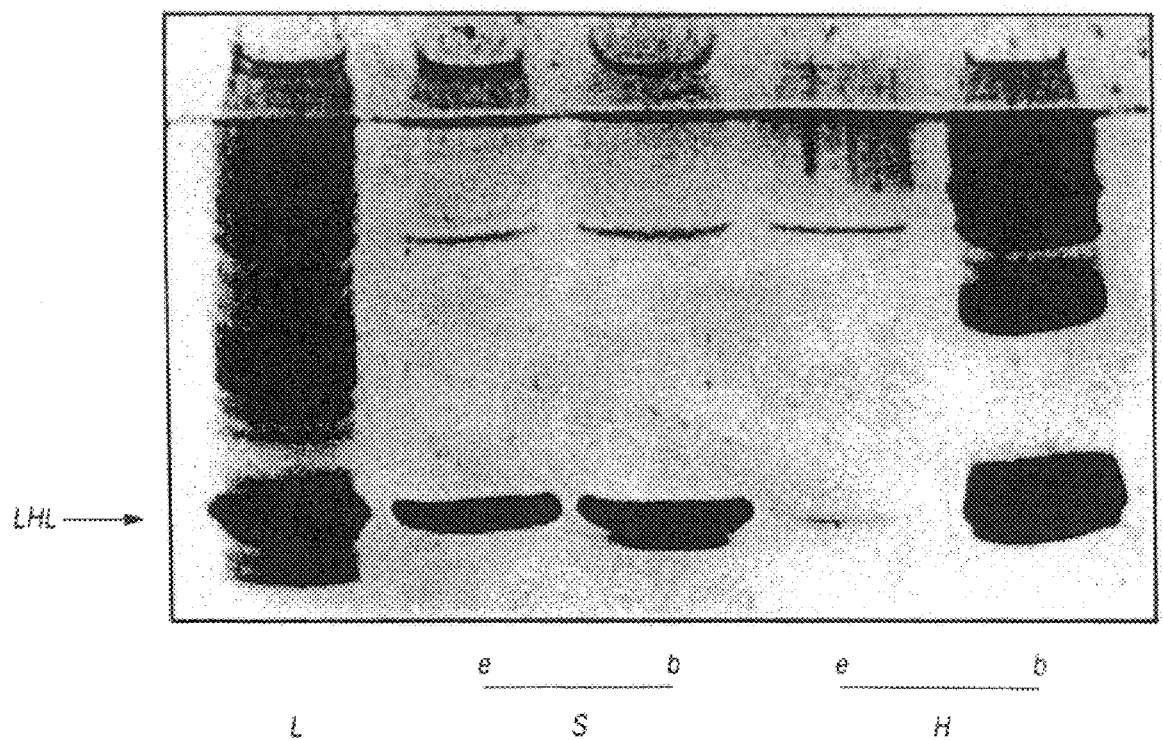

Generation of an LHL Protein Carrying the N-Terminal Flag Epitope and the C-Terminal Strep-Tag A form of LHL (referred to herein as "LHL.seq") was generated by PCR containing the FLAG epitope at its N-terminus and the so called strep-tag at its C-terminus (FIG. 3). The nucleotide and corresponding amino acid sequence for LHL.seq is shown in SEQ ID NO:7 and SEQ ID NO:8, respectively. The FLAG epitope comprises the amino acids DYKDDDDK (SEQ ID NO:9) and the strep-tag the amino acids AWRHPQFGG (SEQ ID NO:14). The FLAG epitope is recognised by several anti-FLAG monoclonal antibodies and the strep-tag by streptavidin. The strep-tag was used for purification of LHL.seq over a streptavidin column. LHL.seq was washed with 0.5% v/v Triton X-100, Tween20 and PBS while bound to the column in order to minimise endotoxin levels. LEL.seq was eluted with either 100 mM glycine pH2.0 or with 1 mg/ml diaminobiotin in PBS. In this method LHL.seq was not purified on the basis of binding immunoglobulin, thereby eliminating potential contamination of other unknown bacterial proteins which also bind immunoglobuliis. The biological activity of LHL.seq, however, remained identical to that of LHL. The FLAG-epitope was added to the N-terminus in order to facilitate the secretion of LHL.seq into the periplasmic space. As in previous expression studies, this was unsuccessful and LHL.seq needed to be purified from total bacterial lysate (FIG. 4). As a result of this, the ompA signal peptide is not removed, which in turn led to formation of LHL.seq multimers.

EXAMPLE 4

Mitogenic Activity of LHL on B Cells

Mitogenic activity of LHL on B cells was tested in overnight cultures of splenocytes and mesenteric lymphocytes ad well as on purified B cells. The activation status of B cells was analysed by FACS, examining B cell size and induction of B7-2 surface expression. LHL's activation potency is similar to LPS (10 μg/ml), a bacterial mitogenic lipopolysaccharide and anti-IgM antibody (25 μg/ml), which crosslinks surface IgM. The results have been independently obtained in several different mouse st e.g. B10.A(4R), CBA, C3H/HeJ and BALB/c. B cells showed a clear dose response to LHL when titrated in 5-fold dilutions (25 μg/ml to 1.6 ng/ml) in the activation assay. The results are shown in FIG. 5. Parallel experiments analysing the T cell activation status within the same cultures demonstrated that LHL has no effect on T cells. T cells did not show any blast formation nor did they upregulate activation markers, e.g. IL2 receptor alpha chain (CD25).

EXAMPLE 5

Blocking of LHL Mitogenicity by HuIgG

In the same experiments, soluble hulgG (500 μg/ml) which binds to the L domains was used to specifically block the activity of LHL. These results rule out that B cell activation was due to a contamination of the bacterially produced LHL with endotoxins. The results are shown in FIG. 6.

EXAMPLE 6

Processing of LHL by B Cells and Presentation of the H Epitope to the Hel-Specific Hybridoma 3A9

Splenocytes or mesenteric lymphocytes were cocultured with the T cell hybridoma 3A9 in the presence of LHL. 3A9 is specific for the HEL peptide 52-61aa presented on MHC II H-2A$^K$. Upon recognition of this peptide, 3A9 secretes IL-2. IL-2 production was measured in a bio assay which evaluates the proliferation of an IL-2 dependent cell line (CTLL) on the basis of ³H-thymidine incorporation during DNA synthesis (FIG. 7). Presentation of H to 3A9 by B cells was clearly demonstrated by the proliferation of the CTLL and could be specifically blocked with huIgG.

EXAMPLE 7

Generation of the Variable (V)-Kappa Light Chain According to the Human LEN Protein Sequence The amino acid sequence of the gene encoding the human myeloma protein LEN was used to generate a variable kappa light chain. This human kappa light chain protein (hereinafter referred to as "kappa") is soluble at relatively high concentrations and has been shown to bind protein L. Kappa was generated from synthetic oligonucleotides by PCR To facilitate protein purification, a FLAG epitope was added to the N-terminus and a strep-tag to the C-terminus (FIG. 8). The nucleotide and amino acid sequence of kappa is shown in SEQ ID NO:10 and 11, respectively.

EXAMPLE 8

Expression of Kappa in E. coli DH10B

Kappa was cloned into pASK75, allowing inducible expression of kappa into the periplasmic space of E. coli. Expression was induced in logarithmically growing cultures of E. coli strain DH10B cells with 400 ng/ml of anhydro-tetracycline for >4 hrs (FIG. 9).

EXAMPLE 9

Purification of Kappa Protein from the Periplasm of DH10B

Cultures were spun down and resuspended in a buffer containing 400 mM sucrose on ice. After 20 min cells were pelleted. Kappa was then purified over an anti-FLAG and/or streptavidin column from the periplasmic fraction (FIG. 10).

EXAMPLE 10

Confirmation of Proper Folding of Kappa After Purification

The proper folding of kappa was demonstrated by its capacity to bind LHL. Kappa was bound to the streptavidin column via its strep-tag This kappa-loaded column was then shown to bind LHL (FIG. 11). The non strep-tag carrying LHL did not bind to the streptavidin column alone.

EXAMPLE 11

Generation of TLHL

TLHL was generated from LHL, kappa and synthetic oligonucleotides encoding a linker connecting kappa and LHL by PCR The linker contained an amino acid sequence corresponding to the tobacco etch virus UEV) protease recognition/cleavage site. All components were cloned into pASK75 resulting in the following protein sequence: FLAG-kappa-linker-TEV-LHL-streptag (FIG. 12). Potentially, TLHL could show similar characteristics as CATAB, since one kappa binding site is blocked and two are required for surface immunoglobulin cross-linking. The nucleotide and amino acid sequences of TLHL are shown in SEQ ID NO:5 and SEQ ID NO:6, respectively.

EXAMPLE 12

Expression of TLHL in DH10B

TLHL expression was induced in logarithmically growing cultures by addition of 400 ng/ml anhydro-tetracycline for >4hrs. TLHL was not secreted into the periplasmic space and caused some cell lysis after induction.

EXAMPLE 13

Purification of TLHL from Total Bacterial Lysate

TLHL was purified via its strep-tag over a streptavidin column from total bacterial lysate (FIG. 13). Endotoxin levels were reduced using the washing protocol earlier described.

EXAMPLE 14

Cleavage of TLHL into "T" and "LHL" with TEV

TLHL was designed so that the kappa portion of the protein could be cleaved off by the TEV protease. The TEV cleavage would generate two polypeptides, each of 172 amino acids. The identical size of the protein fragments is due to TLHL not being secreted into the periplasmic space of E. coli and, therefore, retaining the ompA signal peptide. Incubation of TLHL with the TEV protease in PBS at room temperature or at 4° C. produced therefore, a 19kD band on an SDS-PAGE gel (FIG. 14).

EXAMPLE 15

Assembly of CATAB-TEV from TLHL and Kappa by PCR

CATAB-TFV is assembled from TLHL and kappa by PCR. The TLHL and kappa can be linked by different peptides, for example, TNF amino acids 1–31, that are potential target sites for proteolytic antibodies. In this case, the linker includes a recognition sequence for the tobacco etch virus (TEV) protease which allows the generation of LHL from CATAB-TEV in vitro. The nucleotide and corresponding amino acid sequences of CATAB-TEV are shown in SEQ ID NO:3 and SEQ ED NO:4.

EXAMPLE 16

Expression of CATAB in DH10B and Purification Over a Streptavidin Affinity Column Via Strep-Tag CATAB-TEV is expressed and purified in the same way as TLIL (see above).

EXAMPLE 17

Demonstration of Non-Mitogenic Activity of CATAB-TEV on B Cells

CATAB-TEV is tested in the already established B cell assays which are used to analyse the mitogenic activity of LHL and LHL.seq.

EXAMPLE 18

Revelation of the Mitogenic Activity of CATAB By Proteolytic Cleavage with TEV Protease Digestion of CATAB-TEV with the site specific protease from TEV cleaves the covalent bond between LHL and the kappa domains. This cleavage generates the mitogenic compound LHL which is tested in the standardised B cell activation assays.

EXAMPLE 19

Usage of CATAB in Several Mouse Strains of the K-Haplotype

Several mouse strains are immunised by different routes of administration, e.g. intra-splenic, in order to elicit a catalytic antibody response in vivo. The gld and lpr mutant strains are used as they have been shown to have a relatively high incidence of naturally occurring catalytic auto-antibodies, e.g. antibodies with DNAse activity.

EXAMPLE 20

Detection of CATAB Specific Catalytic Antibodies from the Serum

Serum antibodies from immunised mice are purified for example on a LHL affinity column. Purified antibodies may be incubated with $^{125}$I-labelled CATAB and the proteolytic cleavage is evaluated on PAGE gels. In addition, streptavidin may be used to immobilise CATAB via its C-terminal streptag on 96 well ELISA plates. Immobilised CATAB is proteolytically cleaved by incubation with purified catalytic serum antibodies and an N-terminal affinity tag, e.g. flag epitope, is lost This loss is detected in a sandwich ELISA assay using horse radish peroxidase (HRPO) conjugated antibodies. B cells producing catalytic antibodies can be recovered by standard hybridoma techniques and the catalytic antibodies can be humanised by recombinant DNA technology. For example, "human" antibodies can be derived from humanized mice.

EXAMPLE 21

LHL.seq Induced B7-1 Expression

LHL.seq was tested for its ability to activate B cells as compared to stimulation with anti-IgM and anti-kappa Activation status was measured by the induction of cell surface expression of the activation markers B7-1 and B7-2 and by entry of B cells into cell cycle. Levels of expression of B7-1 and B7-2 were determined by flow cytometry (FACS) with fluorescence labelled monoclonal antibodies while entry into cell cycle was monitored by an increase in cell size by Forward Light Scatter (FSC).

The method employed was as follows. Mesenteric lymphnode cells from C3H/HeJ mice were centrifuged in Nycodenz (1.091 g/cm3) to remove dead cells and red blood cells (rbc). This was followed by 1 hour adherence on plastic at 37° C. to remove adherent cells such as macrophages. Lymph node cells were stimulated in triplicate cultures 3×10$^5$/well in flat bottom 96-well plates in complete RPMI+ 10% FCS medium at 37° C. for 1–3 days. Upregulation of activation markers on B cells was monitored by gating on B220$^-$Thy1$^-$ cells to identify B cells. Stimulation with LPS (20 µg/ml), polyclonal F(ab)$_2$ anti-IgM antibodies (20 µg/ml) and anti-kappa antibodies (10 µg/ml) were included as controls. LHL.seq was used at 1 µg/ml. C3H/HeJ mice were used as source of lymphocytes since this particular mouse strain is non-responsive to LPS. The use of this strain in combination with the LPS control effectively precludes the possibility that B cell stimulation induced by LHL.seq were due to LPS (endotoxin) contamination of the bacterially expressed proteins.

FACS analysis showed that this two day stimulation of C3H/HeJ lymph node cells with LPS did not result in B cell activation whereas stimulation with either anti-IgM antibodies, anti-kappa antibodies or LHL.seq did as measured by an increased FSC and upregulation of B7-2. The characteristic potency of LHL.seq is demonstrated by the strong induction of B7-1 expression after incubation (see FIG. 15). Anti-IgM induces B7-1 on day 2–3 of stimulation.

EXAMPLE 22

LHL.seq Induced MHC Class II

LHL.seq was compared in its potential to ensure proper upregulation of MHC class II on stimulated B cells. Anti-IgM antibodies (20 µg/ml) as well as LHL. seq (1 µg/ml) blocked with huIgG (500 µg/ml) were included as controls. The method used was as described in Example 21.

Upregulation of MHC Class II molecules on B cells is a prerequisite to receive T cell help in vivo.

Overnight stimulation of C3H/HeJ lymph node cells with anti-Igm antibodies as well as LHL.seq did result in increased FSC and upregulation of MHC class II. LHL.seq's activities were completely blocked by addition of 500 µg/ml huIgG to the cultures (see FIG. 16).

EXAMPLE 23

LHL.seq Induced Proliferation in a Dose Dependent Fashion

Serial dilutions of LHL.seq were used to stimulate B cell proliferation. The experiment demonstrated that LHL.seq's biological properties are similar to conventional B cell mitogens like anti-IgM antibodies. Thus, dose-response curves for stimulation of either mesenteric lymphnode cells from C3H/HeJ and splenocytes from CBA/J were obtained (see FIG. 17).

EXAMPLE 24

TLHL Induced B Cell Activation

LHL.seq, TLHL and TEV-cleaved TLHL were tested for their ability to activate B cells as mered by the induction of cell surface expression of the activation markers B7- 1 (CD86) and B7-2 (CD80) and by entry of B cells into cell cycle. Levels of expression of B7-1 and B7-2 were determined by flow cytometry (FACS) with fluorescence-labelled monoclonal antibodies while proliferation was monitored by an increase in cell size by Forward Light Scatter (FSC) and by $^3$H-thymidine-uptake assays.

The method employed as described in Example 21.

Overnight stimulation of C3H/HeJ lymph node cells with LPS did not result in B cell activation whereas stimulation with either anti-TgM antibodies or LHL.seq did as measured by an increased FSC and upregulation of B7-2. The characteristic potency of LHL.seq is demonstrated by the strong induction of B7-1 expression after overnight incubation (see FIG. 18). Anti-IgM induces B7-1 on day 2–3 of stimulation.

TLHL, however, activated B cells to the same extent as LHL.seq. This was unexpected since it was presumed that blocking one L domain with a covalently linked kappa would prevent crosslinking of immunoglobulin on the B cell surface. Prevention of crosslinking should result in no or significantly lower B cell activation than that achieved with equal amounts of LHL.seq. TEV-cleaved TLHL, which results in omp-kappa (see below) plus the LHL.seq part, gave much lower B cell activation than uncleaved TLHL as indicated by less B7-1 and B7-2 upregulation and lower FSC increase (FIG. 18).

Splenocytes from CBA/J mice were centrifuged in Nycodenz (1.091 g/cm$^3$) to remove dead cells and rbc. This was followed by 1 hour adherence on plastic at 37° C. to remove adherent cells. Splenocytes were then stimulated in triplicate cultures at 2×10$^5$/well in flat bottom 96-well plates in complete RPMI+10% v/v FCS medium at 37° C. for 2 days. Cells were pulsed for the last 6 hours with $^3$H-thymidine. DNA was then harvested onto glassfibre filters and incorporation of $^3$H-thymidine was measured in a β-counter.

The results obtained by FACS analysis were confirmed by the proliferation data; TLHL and LHL.seq induced equivalent B cell proliferation while TEV-cleaved TLHL was about 70% less potent (FIG. 19).

EXAMPLE 25

TEV-Cleaved TLHL Stimulation Data Confirm Omp Induced Multimerisation

The B cell activation data lead the inventors to the conclusion that both LHL, LHL.seq and TLHL exist in solution as multimeric molecules. While dimeric or oligomeric immunoglobulin-binding molecules such as anti-IgM antibodies induce B cell activation, multimers such as anti-IgD-dextran result in a significantly higher degree of B cell activation. This is also the case with LHL, LHL.seq and TLHL in the above experiments as demonstrated by the extensive upregulation of B7-1 after overnight culture. The multimerisation is facilitated by the ompA signal peptide (omp). It has been published by others that the ompa signal peptide forms multimers in aqueous solution. Evidence for LHL, LHL.seq and TLHL aggregation has also been obtained in HPLC studies.

A new recombinant LHL.seq protein lacking the ompA signal peptide, called LHL-omp, was engineered which also confirms these conclusions (see below).

EXAMPLE 26

TLHL Multimerisation Overcomes "Kappa-Blocking"

Although one 'L' domain should be blocked by kappa in TLHL, the multimerisation mediated by the omp allows several free 'L' domains to exist in one multimeric molecule $[TLHL]_n$. This will lead to extentive sIg crosslinking and full B cell activation as demonstrated.

EXAMPLE 27

Generation and Analysis of LHL-Omp

LHL-omp was generated from LHL.seq via PCR with the proofreading polymerase Pfu eliminating the ompA signal sequence.

EXAMPLE 28

Affinity Column Purification of LHL-Omp

Although LHL-omp contains a Strep-tag, it could not be purified via the Streptavidin column using the standard protocol, indicating a lower avidity to the column matrix than that of LHL.seq. This lower avidity confirms the multimerisation of LHL.seq via omp, being the only difference between LHL.seq and LHL-omp. In agreement with this LHL-omp was readily purified over a huIgG affinity column (FIG. 20).

EXAMPLE 29

LHL-Omp Induced B Cell Activation

The ability of LHL-omp to induce B cell activation was assessed by incubating splenocytes from C3H/HeJ mice for varying periods of time before analysing B7-1 and B7-2 expression levels on B cells as outlined above. The progression of B cells into cell cycle was monitored by FACS and proliferation assays.

Cells were prepared and cultured as described above. LPS (20 µg/ml) and anti-IgM (20 µg/ml) were used as controls. Stimulation of C3H/HeJ splenocytes with LPS did not result in detectable B cell activation whereas treatment with either anti-IgM antibodies or LHL.seq induced B cell activation during overnight culture; increased FSC and B7-2 upregulation for anti-IgM antibodies and increased FSC and B7-1 and B7-2 expression for LHL.seq. LHL-omp, used at 2 µg/ml, was less potent than LHL.seq in inducing upregulation of B7-1, B7-2 and blasting of B cells, as indicated by the FSC profile. The unchanged FSC profile indicated that LHL-omp did not induce B cell proliferation (see FIG. 21). This was confirmed in proliferation assays (FIG. 22).

B cells were stimulated simultaneously with LHL-omp and anti-CD40 antibodies (mAb FGK45.5 at a concentration of 0.5 µg/ml). Anti-CD40 antibodies served as a partial substitute for T cell help. The combination of sIg and helper T cell like signaling achieved good levels of B cell activation and proliferation. This could especially be demonstrated when using LHL-omp at a concentration of 125 ng/ml. 125 ng/ml induced no B cell activation on its own, however, when used in combination with the anti-CD40 antibody, which by itself is also of low potency, B7-1, B7-2 add FSC upregulation were achieved. Suggesting that LHL-omp and anti-CD40 antibodies can act synergistically (see FIG. 21).

EXAMPLE 30

Utilising Omp to Design a Novel Multimeric Mitogen

Experimental data obtained show that the signal peptide from the outer membrane protein A (ompA) of *E. coli* induces aggregation of the recombinant proteins LHL.seq and TLHL. The ompA signal peptide (omp) is usually cleaved off once the protein reaches its destination, the bacterial periplasmic space. In the case of LHL, LHL.seq and TLHL, however, the secretion into the periplasm is impaired. All three proteins remain in the cytoplasm and the omp peptide forms their N-terminal part. The N-terminal omp peptide induces multimerisation as demonstrated by the potentiation of their biological activity as compared to the recombinant protein LHL-omp and TEV-cleaved TLHL.

The observation that omp induces multimerisation allows the design of simpler molecules with the same desired biological fiction as LHL, TLHL and CATAB. For this purpose we propose the following protein design. Above results demonstrate that the proteins described are not secreted into the periplasmic space. It should therefore be possible to produce proteins that have an omp peptide as their N-terminal part and L or HL as their C-terminal part. As omp allows the formation of multimers, this should result in the formation of $[ompL]_n$, hereafter called ompL, or $[ompHL]_n$ where n is equal or larger than 2 (see FIG. 23).

EXAMPLE 31

Multimerisation of OmpL and Design of FV-CATAB

Multimerisation of ompL generates a protein complex that should allow crosslinking of surface immunoglobulins in a similar fashion to LHL or LHL.seq. OmpL itself, however, is a relatively simple monomeric protein which needs only a single blocking entity. This blocking domain will be the below described scdsFv resulting the fusion protein ompL-linker-TEV-scdsFv (Fv-catAb). The reverse of this configuration, scdsFv-TEV-linker-Lomp (pFv-catAb) will also be generated, as this might allow for periplasmic secretion of pFv-catAb. The latter pFv-catAb requires the functional multimerisation and biological activity of Lomp, a protein with the reverse fusion order of ompL and the omp peptide at its C-terminal (see FIG. 24). All described recombinant proteins are tested in the experimental systems outlined above.

EXAMPLE 32

Redesign of the L Domain Blocking Entity

Two potential problems are associated with the use of the LEN kappa light chain as a blocking domain for L. First, proteins (ie. LHL, LHL.seq and TLHL) are not secreted into the periplasmic space during expression in *E. coli,* which might cause folding problems in the kappa portion. Secondly, there are no direct means of purifying proteins with potentially correctly folded kappas in the described system, as antibodies against kappa would be bound by LHL.seq.

In order to allow for purification of correctly folded growth factor precursors, the blocking entity was therefore redesigned. Kappa will be replaced by a single chain (sc) antibody which is stabilised by an internal disulfide bridge (disulfide bridge stabilised, ds). This scdsFv will be derived from the extensively described plasmacytoma McPc603 with anti-phosphorylcholine specificity. The phosphorylcholine-binding ability will facilitate the purification of correctly folded recombinant proteins via a phosphorylcholine affinity column (see FIG. 24).

EXAMPLE 33

Potential Use of LHL/CATAB Derivatives in Humans

In order to enable production of catalytic antibodies in humans, slight modifications of the constructs need to be performed. The 'H' T cell epitope has to be exchanged for an "universal T cell epitope" which will be recognised by T cells in the majority of humans in conjunction with their more diverse MHC class II molecules.

Those skilled in the art will appreciate that the invention described herein is susceptible to variations and modifications other than hose specifically described. It is to be understood that the invention includes all such variations and modifications. The invention also includes all of the steps, features, compositions and compounds referred to or indicated in this specification, individually or collectively, and any and all combinations of any two or more of said steps or features.

---

What is claimed is:

1. A recombinant or synthetic growth factor precursor comprising a B cell surface molecule binding portion wherein a catalytic product of said precursor is capable of inducing B cell mitogenesis.

2. The recombinant or synthetic growth factor precursor of claim 1 further comprising a portion capable of providing T cell dependent help for a B cell.

3. The recombinant or synthetic growth factor precursor of claim 2 wherein the B cell surface molecule binding portion comprises a B cell surface immunoglobulin binding domain and the portion providing T cell dependent help for a B cell is a T cell epitope.

4. The recombinant or synthetic growth factor precursor of claim 2 wherein the growth factor precursor comprises at least two B cell surface binding portions which facilitate cross-linking of B cell surface binding molecules.

5. The recombinant or synthetic growth factor precursor of any one of claim 1 or 2 or 3 or 4 further comprising a portion to facilitate multimerization of said precursor.

6. The recombinant synthetic growth factor precursor of claim 5 wherein said multimer facilitating portion is a signal peptide.

7. The recombinant synthetic growth factor precursor of claim 6 wherein the signal peptide is from ompA or a functional equivalent thereof.

8. The recombinant or synthetic growth factor precursor of claim 3 wherein the B cell surface immunoglobulin binding domain is protein L from *Peptostreptococcus magnus* or a derivative thereof or a functional equivalent thereof.

9. The recombinant or synthetic growth factor precursor of claim 3 wherein the T cell epitope is hen egg lysozyme (HEL) or a derivative thereof or a functional equivalent thereof.

10. The recombinant or synthetic growth factor precursor of claim 1, further comprising an antigen linked to said B cell surface immunoglobulin binding portion such that upon cleavage of said antigen or a region proximal to said antigen, said recombinant or synthetic growth factor induces B cell mitogenesis.

11. The recombinant or synthetic growth factor precursor of claim 10 comprising an amino acid sequence substantially as set forth in SEQ ID NO:2 or having at least 60% similarity thereto.

12. The recombinant or synthetic growth factor precursor of claim 10 comprising an amino acid sequence substantially as set forth in SEQ ID NO:4 or having at least 60% similarity thereof.

13. A composition of matter capable of inducing B cell mitogenesis said composition of matter comprising components selected from:

(i) a recombinant or synthetic molecule comprising a B cell surface immunoglobulin binding portion;

(ii) a recombinant or synthetic molecule in multimeric form comprising a B cell surface molecule binding portion;

(iii) a recombinant or synthetic molecule of (i) or (ii) comprising a portion providing T cell dependent help for a B cell; and (iv) separate compositions mixed prior to use or used sequentially or simultaneously comprising in a first composition a molecule having a B cell surface molecule binding portion and in a second composition a molecule capable of providing T cell dependent help for a B cell.

14. The composition of matter of claim 13 wherein the molecule providing T cell dependent help for a B cell is a T cell epitope or an anti-CD40 antibody or a functional equivalent thereof.

15. The recombinant or synthetic growth factor precursor of claim 1 having the structure:

$$MX_1(X_2)_b$$

wherein:

$X_1$ is a B cell surface molecule binding entity such as a B cell surface immunoglobulin binding entity;

$X_2$ is a portion providing T cell dependent help for a B cell;

M is a portion enabling or facilitating multimer formation of the recombinant or synthetic molecule; and b represents the number of $X_2$ molecules and may be 0, 1 or >1.

16. The recombinant or synthetic growth factor precursor of claim 1 having the structure:

$$(M)_cAX_1(X_2)_d(X_3)_eA(M)_f$$

wherein:

A is a target antigen or which a catalytic antibody is sought;

$X_1$ and $X_3$ may be the same or different and each is a B cell surface molecule binding entity;

$X_2$ is a portion providing T cell dependent help for a B cell;

M is a portion facilitating multimer formation of the recombinant or synthetic molecule;

c and may be the same or different and each is 0, 1 or >1;

e is 0 or 1 with the proviso that if both c and f are 0 then e cannot be 0;

d is 0 or 1 or >1; wherein a catalytic antibody on the surface of said B cell is capable of cleaving all or a portion of A from said recombinant or synthetic molecule, wherein said resulting catalytic product is capable of inducing B cell mitogenesis.

17. The recombinant or synthetic growth factor precursor of claim 1 comprising the structure:

$$I'AX_1X_2X_3AI''$$

wherein:

A is a target antigen for which a catalytic antibody is sought;

$X_1$ and $X_3$ may be the same or different and each is a B cell surface molecule binding entity;

I' and I" are optionally present and may be the same or different and each is a blocking reagent for Xi and $X_3$;

$X_2$ is a portion providing T cell dependent help for a B cell;

wherein a catalytic antibody on the surface of said B cell is capable of cleaving all or part of A from said recombinant or synthetic molecule resulting in the molecule $(A)X_1X_2X_3(A')$ wherein A' is optionally present and is a portion of A after cleavage with the catalytic antibody wherein said resulting molecule is capable of inducing T cell dependent B cell mitogenesis of the B cell to which $X_1$ and $X_3$ bind.

18. A pharmaceutical composition comprising the recombinant or synthetic growth factor precursor of claim 1 or 15 or 16 or 17 or 29 or 30 and one or more pharmaceutically carriers and/or diluents.

19. The recombinant or synthetic growth factor precursor of claim 1 which comprises the structure:

$$(I'AX_1(X_2')_o(X_2X_3AI'')_n)_m$$

wherein:

I' and I" may be the same or different and each is a blocking reagent for $X_1$ and $X_3$ such as a kappa or lambda light chain or an sc-ds-Fv;

A is the target antigen for which a catalytic antibody is sought;

$X_1$ and $X_3$ are B cell surface molecule binding entities;

$X_2$ and $X_2$' may be the same or different and each is an entity capable or providing T cell dependent help for a B cell;

o may be 0 or 1;

n indicates the multimeric nature of the component in parentheses and may be 0, 1 or >1;

m indicates the multimeric nature of the component in parenthesis and may be 1 or >1.

20. The recombinant or synthetic growth factor precursor of claim 1 which comprises the structure:

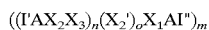

wherein:

I' and I" may be the same or different and each is a blocking reagent for $X_1$ and $X_3$ such as a kappa or lambda light chain or an sc-ds-Fv;

A is the target antigen for which a catalytic antibody is sought;

$X_1$ and $X3$ are B cell surface molecule binding entities;

$X_2$ and $X_2$' may be the same or different and each is an entity capable or providing T cell dependent help for a B cell;

o may be 0 or 1;

n indicates the multimeric nature of the component in parentheses and may be 0, 1 or >1;

m indicates the multimeric nature of the component in parenthesis and may be 1 or >1.

* * * * *

UNITED STATES PATENT AND TRADEMARK OFFICE
CERTIFICATE OF CORRECTION

PATENT NO. : 6,521,741 B1
DATED : February 18, 2003
INVENTOR(S) : Frank Koentgen et al.

It is certified that error appears in the above-identified patent and that said Letters Patent is hereby corrected as shown below:

<u>Title page,</u>
Item [73], "Frank Koentgen Pty Ltd." should read -- Frank Koentgen --
Item [30], "8951/96" should read -- PN8951/96 -- and "5375/97" should read -- PO5375/97 --

Signed and Sealed this

Twenty-seventh Day of January, 2004

JON W. DUDAS
*Acting Director of the United States Patent and Trademark Office*

SEQUENCE LISTING (1) GENERAL INFORMATION:

(iii) NUMBER OF SEQUENCES: 14

(2) INFORMATION FOR SEQ ID NO: 1:

(i) SEQUENCE CHARACTERISTICS:
      (A) LENGTH: 548 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: CDS
      (B) LOCATION: 1..548

(xi) SEQUENCE DESCRIPTION: SEQ ID NO: 1:

```
ATG AAA AAG ACA GCT ATC GCG ATT GCA GTG GCA CTG GCT GGT TTC GCT      48
Met Lys Lys Thr Ala Ile Ala Ile Ala Val Ala Leu Ala Gly Phe Ala
 1               5                  10                  15

ACC GTA GCG CAG GCC GCT CCG AAA GAT AAC ACG GAA GAA GTC ACG ATC      96
Thr Val Ala Gln Ala Ala Pro Lys Asp Asn Thr Glu Glu Val Thr Ile
             20                  25                  30

AAA GCG AAC CTG ATC TTT GCA AAT GGT AGC ACA CAA ACT GCA GAA TTC     144
Lys Ala Asn Leu Ile Phe Ala Asn Gly Ser Thr Gln Thr Ala Glu Phe
         35                  40                  45

AAA GGT ACC TTC GAA AAA GCG ACC TCG GAA GCT TAT GCG TAT GCA GAT     192
Lys Gly Thr Phe Glu Lys Ala Thr Ser Glu Ala Tyr Ala Tyr Ala Asp
     50                  55                  60

ACT TTG AAG AAA GAC AAT GGT GAA TAT ACT GTA GAT GTT GCA GAT AAA     240
Thr Leu Lys Lys Asp Asn Gly Glu Tyr Thr Val Asp Val Ala Asp Lys
 65                  70                  75                  80

GGT TAC ACC CTG AAC ATC AAA TTC GCG GGT AAA GAA GCG ACC AAC CGT     288
Gly Tyr Thr Leu Asn Ile Lys Phe Ala Gly Lys Glu Ala Thr Asn Arg
                 85                  90                  95
```

```
AAC ACC GAC GGT TCC ACC GAC TAC GGT ATC TTA CAG ATC AAC TCT CGT       336
Asn Thr Asp Gly Ser Thr Asp Tyr Gly Ile Leu Gln Ile Asn Ser Arg
            100                 105                 110

TGG GGT GGT CTG ACC CTG AAA GAA GAA GTC ACG ATC AAA GCG AAC CTG       384
Trp Gly Gly Leu Thr Leu Lys Glu Glu Val Thr Ile Lys Ala Asn Leu
        115                 120                 125

ATC TTT GCA AAT GGT AGC ACA CAA ACT GCA GAA TTC AAA GGT ACC TTC       432
Ile Phe Ala Asn Gly Ser Thr Gln Thr Ala Glu Phe Lys Gly Thr Phe
    130                 135                 140

GAA AAA GCG ACC TCG GAA GCT TAT GCG TAT GCA GAT ACT TTG AAG AAA       480
Glu Lys Ala Thr Ser Glu Ala Tyr Ala Tyr Ala Asp Thr Leu Lys Lys
145                 150                 155                 160

GAC AAT GGT GAA TAT ACT GTA GAT GTT GCA GAT AAA GGT TAC ACC CTG       528
Asp Asn Gly Glu Tyr Thr Val Asp Val Ala Asp Lys Gly Tyr Thr Leu
                165                 170                 175

AAC ATC AAA TTC GCG GGT   TA                                          548
Asn Ile Lys Phe Ala Gly
                180

(2) INFORMATION FOR SEQ ID NO: 2:

(i) SEQUENCE CHARACTERISTICS:
        (A) LENGTH: 182 amino acids
        (B) TYPE: amino acid
        (D) TOPOLOGY: linear (ii) MOLECULE TYPE: protein (xi) SEQUENCE DESCRIPTION: SEQ ID NO: 2:

Met Lys Lys Thr Ala Ile Ala Ile Ala Val Ala Leu Ala Gly Phe Ala
  1               5                  10                  15

Thr Val Ala Gln Ala Ala Pro Lys Asp Asn Thr Glu Glu Val Thr Ile
                20                  25                  30

Lys Ala Asn Leu Ile Phe Ala Asn Gly Ser Thr Gln Thr Ala Glu Phe
            35                  40                  45

Lys Gly Thr Phe Glu Lys Ala Thr Ser Glu Ala Tyr Ala Tyr Ala Asp
        50                  55                  60

Thr Leu Lys Lys Asp Asn Gly Glu Tyr Thr Val Asp Val Ala Asp Lys
 65                  70                  75                  80

Gly Tyr Thr Leu Asn Ile Lys Phe Ala Gly Lys Ala Thr Asn Arg
                    85                  90                  95

Asn Thr Asp Gly Ser Thr Asp Tyr Gly Ile Leu Gln Ile Asn Ser Arg
            100                 105                 110

Trp Gly Gly Leu Thr Leu Lys Glu Glu Val Thr Ile Lys Ala Asn Leu
        115                 120                 125

Ile Phe Ala Asn Gly Ser Thr Gln Thr Ala Glu Phe Lys Gly Thr Phe
    130                 135                 140

Glu Lys Ala Thr Ser Glu Ala Tyr Ala Tyr Ala Asp Thr Leu Lys Lys
145                 150                 155                 160

Asp Asn Gly Glu Tyr Thr Val Asp Val Ala Asp Lys Gly Tyr Thr Leu
                165                 170                 175

Asn Ile Lys Phe Ala Gly
                180

(2) INFORMATION FOR SEQ ID NO: 3:

(i) SEQUENCE CHARACTERISTICS:
        (A) LENGTH: 1490 base pairs
        (B) TYPE: nucleic acid
```

(C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..1490

(xi) SEQUENCE DESCRIPTION: SEQ ID NO: 3:

```
ATG AAA AAG ACA GCT ATC GCG ATT GCA GTG GCA CTG GCT GGT TTC GCT        48
Met Lys Lys Thr Ala Ile Ala Ile Ala Val Ala Leu Ala Gly Phe Ala
 1               5                  10                  15

ACC GTA GCG CAG GCC GAC TAC AAG GAC GAT GAC GAC AAG GAT ATC GTG        96
Thr Val Ala Gln Ala Asp Tyr Lys Asp Asp Asp Asp Lys Asp Ile Val
                20                  25                  30

ATG ACC CAG TCT CCA GAC TCC CTG GCT GTG TCT CTG GGC GAG CGT GCC       144
Met Thr Gln Ser Pro Asp Ser Leu Ala Val Ser Leu Gly Glu Arg Ala
             35                  40                  45

ACC ATC AAT TGC AAG TCC AGC CAG AGT GTT TTA TAC AGC TCC AAC AGC       192
Thr Ile Asn Cys Lys Ser Ser Gln Ser Val Leu Tyr Ser Ser Asn Ser
         50                  55                  60

AAG AAC TAC CTG GCT TGG TAC CAG CAG AAA CCA GGT CAG CCT CCT AAG       240
Lys Asn Tyr Leu Ala Trp Tyr Gln Gln Lys Pro Gly Gln Pro Pro Lys
 65                  70                  75                  80

CTG CTC ATT TAC TGG GCA TCT ACC CGT GAA TCC GGC GTT CCT GAC CGT       288
Leu Leu Ile Tyr Trp Ala Ser Thr Arg Glu Ser Gly Val Pro Asp Arg
                 85                  90                  95

TTC AGT GGT AGC GGT TCT GGT ACA GAT TTC ACT CTC ACC ATC AGC AGC       336
Phe Ser Gly Ser Gly Ser Gly Thr Asp Phe Thr Leu Thr Ile Ser Ser
                100                 105                 110

CTC CAG GCT GAA GAT GTG GCA GTT TAT TAC TGC CAG CAG TAT TAC AGT       384
Leu Gln Ala Glu Asp Val Ala Val Tyr Tyr Cys Gln Gln Tyr Tyr Ser
            115                 120                 125

ACC CCG TAC TCC TTC GGT CAG GGT ACC AAA CTG GAA ATC AAA CGC TCC       432
Thr Pro Tyr Ser Phe Gly Gln Gly Thr Lys Leu Glu Ile Lys Arg Ser
        130                 135                 140                 145

GGT AGC GGT GGC GGT GGT TCT GGT GGT GGT GGG AGC TCT GGT GGT GGC       480
Gly Ser Gly Gly Gly Gly Ser Gly Gly Gly Gly Ser Ser Gly Gly Gly
                150                 155                 160

TCT GGT GGT GGT AGC GAA AAC CTG TAC TTC CAG GGT GGT AGC GCC GAA       528
Ser Gly Gly Gly Ser Glu Asn Leu Tyr Phe Gln Gly Gly Ser Ala Glu
                165                 170                 175

GAA GTC ACG ATC AAA GCG AAC CTG ATC TTT GCA AAT GGT AGC ACA CAA       576
Glu Val Thr Ile Lys Ala Asn Leu Ile Phe Ala Asn Gly Ser Thr Gln
            180                 185                 190

ACT GCA GAA TTC AAA GGT ACC TTC GAA AAA GCG ACC TCG GAA GCT TAT       624
Thr Ala Glu Phe Lys Gly Thr Phe Glu Lys Ala Thr Ser Glu Ala Tyr
        195                 200                 205                 210

GCG TAT GCA GAT ACT TTG AAG AAA GAC AAT GGT GAA TAT ACT GTA GAT       672
Ala Tyr Ala Asp Thr Leu Lys Lys Asp Asn Gly Glu Tyr Thr Val Asp
                215                 220                 225

GTT GCA GAT AAA GGT TAC ACC CTG AAC ATC AAA TTC GCG GGT AAA GAA       720
Val Ala Asp Lys Gly Tyr Thr Leu Asn Ile Lys Phe Ala Gly Lys Glu
            230                 235                 240

GCG ACC AAC CGT AAC ACC GAC GGT TCC ACC GAC TAC GGT ATC TTA CAG       768
Ala Thr Asn Arg Asn Thr Asp Gly Ser Thr Asp Tyr Gly Ile Leu Gln
        245                 250                 255

ATC AAC TCT CGT TGG GGT GGT CTG ACC AGC GCC GAA GAA GTC ACG ATC       816
Ile Asn Ser Arg Trp Gly Gly Leu Thr Ser Ala Glu Glu Val Thr Ile
260                 265                 270                 275
```

-continued

| | | |
|---|---|---|
| AAA GCG AAC CTG ATC TTT GCA AAT GGT AGC ACA CAA ACT GCA GAA TTC | | 864 |
| Lys Ala Asn Leu Ile Phe Ala Asn Gly Ser Thr Gln Thr Ala Glu Phe | | |
| 280 285 290 | | |
| | | |
| AAA GGT ACC TTC GAA AAA GCG ACC TCG GAA GCT TAT GCG TAT GCA GAT | | 912 |
| Lys Gly Thr Phe Glu Lys Ala Thr Ser Glu Ala Tyr Ala Tyr Ala Asp | | |
| 295 300 305 | | |
| | | |
| ACT TTG AAG AAA GAC AAT GGT GAA TAT ACT GTA GAT GTT GCA GAT AAA | | 960 |
| Thr Leu Lys Lys Asp Asn Gly Glu Tyr Thr Val Asp Val Ala Asp Lys | | |
| 310 315 320 | | |
| | | |
| GGT TAC ACC CTG AAC ATC AAA TTC GCG GGT AAA GAA AGC GGT GGC GGT | | 1008 |
| Gly Tyr Thr Leu Asn Ile Lys Phe Ala Gly Lys Glu Ser Gly Gly Gly | | |
| 325 330 335 | | |
| | | |
| GGT TCT GGT GGT GGT GGG AGC GGC GCC GGT GGT GGC TCT GGT GGT GGT | | 1056 |
| Gly Ser Gly Gly Gly Gly Ser Gly Ala Gly Gly Gly Ser Gly Gly Gly | | |
| 340 345 350 355 | | |
| | | |
| AGC GAA AAC CTG TAC TTC CAG GGT GGT GGC GGT GGC AGC GGC GGT GGT | | 1104 |
| Ser Glu Asn Leu Tyr Phe Gln Gly Gly Gly Gly Gly Ser Gly Gly Gly | | |
| 360 365 370 | | |
| | | |
| GGT GAT ATC GTG ATG ACC CAG TCT CCA GAC TCC CTG GCT GTG TCT CTG | | 1152 |
| Gly Asp Ile Val Met Thr Gln Ser Pro Asp Ser Leu Ala Val Ser Leu | | |
| 375 380 385 | | |
| | | |
| GGC GAG CGT GCC ACC ATC AAT TGC AAG TCC AGC CAG AGT GTT TTA TAC | | 1200 |
| Gly Glu Arg Ala Thr Ile Asn Cys Lys Ser Ser Gln Ser Val Leu Tyr | | |
| 390 395 400 | | |
| | | |
| AGC TCC AAC AGC AAG AAC TAC CTG GCT TGG TAC CAG CAG AAA CCA GGT | | 1248 |
| Ser Ser Asn Ser Lys Asn Tyr Leu Ala Trp Tyr Gln Gln Lys Pro Gly | | |
| 405 410 415 | | |
| | | |
| CAG CCT CCT AAG CTG CTC ATT TAC TGG GCA TCT ACC CGT GAA TCC GGC | | 1296 |
| Gln Pro Pro Lys Leu Leu Ile Tyr Trp Ala Ser Thr Arg Glu Ser Gly | | |
| 420 425 430 435 | | |
| | | |
| GTT CCT GAC CGT TTC AGT GGT AGC GGT TCT GGT ACA GAT TTC ACT CTC | | 1344 |
| Val Pro Asp Arg Phe Ser Gly Ser Gly Ser Gly Thr Asp Phe Thr Leu | | |
| 440 445 450 | | |
| | | |
| ACC ATC AGC AGC CTC CAG GCT GAA GAT GTG GCA GTT TAT TAC TGC CAG | | 1392 |
| Thr Ile Ser Ser Leu Gln Ala Glu Asp Val Ala Val Tyr Tyr Cys Gln | | |
| 455 460 465 | | |
| | | |
| CAG TAT TAC AGT ACC CCG TAC TCC TTC GGT CAG GGT ACC AAA CTG GAA | | 1440 |
| Gln Tyr Tyr Ser Thr Pro Tyr Ser Phe Gly Gln Gly Thr Lys Leu Glu | | |
| 470 475 480 | | |
| | | |
| ATC AAA CGC AGC GGT AGC GCT TGG CGT CAC CCG CAG TTC GGT GGT TAA | | 1490 |
| Ile Lys Arg Ser Gly Ser Ala Trp Arg His Pro Gln Phe Gly Gly * | | |
| 485 490 495 500 | | |

(2) INFORMATION FOR SEQ ID NO: 4:

(i) SEQUENCE CHARACTERISTICS:
        (A) LENGTH: 496 amino acids
        (B) TYPE: amino acid
        (D) TOPOLOGY: linear (ii) MOLECULE TYPE: protein (xi) SEQUENCE DESCRIPTION: SEQ ID NO: 4:

Met Lys Lys Thr Ala Ile Ala Ile Ala Val Ala Leu Ala Gly Phe Ala
1               5                   10                  15

Thr Val Ala Gln Ala Asp Tyr Lys Asp Asp Asp Lys Asp Ile Val
            20                  25                  30

Met Thr Gln Ser Pro Asp Ser Leu Ala Val Ser Leu Gly Glu Arg Ala
            35                  40                  45

Thr Ile Asn Cys Lys Ser Ser Gln Ser Val Leu Tyr Ser Ser Asn Ser
        50                  55                  60

```
Lys Asn Tyr Leu Ala Trp Tyr Gln Gln Lys Pro Gly Gln Pro Pro Lys
 65                  70                  75                  80

Leu Leu Ile Tyr Trp Ala Ser Thr Arg Glu Ser Gly Val Pro Asp Arg
                 85                  90                  95

Phe Ser Gly Ser Gly Ser Gly Thr Asp Phe Thr Leu Thr Ile Ser Ser
            100                 105                 110

Leu Gln Ala Glu Asp Val Ala Val Tyr Tyr Cys Gln Gln Tyr Tyr Ser
        115                 120                 125

Thr Pro Tyr Ser Phe Gly Gln Gly Thr Lys Leu Glu Ile Lys Arg Ser
    130                 135                 140

Gly Ser Gly Gly Gly Gly Ser Gly Gly Gly Gly Ser Ser Gly Gly Gly
145                 150                 155                 160

Ser Gly Gly Gly Ser Glu Asn Leu Tyr Phe Gln Gly Gly Ser Ala Glu
                165                 170                 175

Glu Val Thr Ile Lys Ala Asn Leu Ile Phe Ala Asn Gly Ser Thr Gln
            180                 185                 190

Thr Ala Glu Phe Lys Gly Thr Phe Glu Lys Ala Thr Ser Glu Ala Tyr
        195                 200                 205

Ala Tyr Ala Asp Thr Leu Lys Lys Asp Asn Gly Glu Tyr Thr Val Asp
    210                 215                 220

Val Ala Asp Lys Gly Tyr Thr Leu Asn Ile Lys Phe Ala Gly Lys Glu
225                 230                 235                 240

Ala Thr Asn Arg Asn Thr Asp Gly Ser Thr Asp Tyr Gly Ile Leu Gln
                245                 250                 255

Ile Asn Ser Arg Trp Gly Gly Leu Thr Ser Ala Glu Glu Val Thr Ile
            260                 265                 270

Lys Ala Asn Leu Ile Phe Ala Asn Gly Ser Thr Gln Thr Ala Glu Phe
        275                 280                 285

Lys Gly Thr Phe Glu Lys Ala Thr Ser Glu Ala Tyr Ala Tyr Ala Asp
    290                 295                 300

Thr Leu Lys Lys Asp Asn Gly Glu Tyr Thr Val Asp Val Ala Asp Lys
305                 310                 315                 320

Gly Tyr Thr Leu Asn Ile Lys Phe Ala Gly Lys Glu Ser Gly Gly Gly
                325                 330                 335

Gly Ser Gly Gly Gly Ser Gly Ala Gly Gly Ser Gly Gly Gly
            340                 345                 350

Ser Glu Asn Leu Tyr Phe Gln Gly Gly Gly Ser Gly Gly Gly
    355                 360                 365

Gly Asp Ile Val Met Thr Gln Ser Pro Asp Ser Leu Ala Val Ser Leu
370                 375                 380

Gly Glu Arg Ala Thr Ile Asn Cys Lys Ser Ser Gln Ser Val Leu Tyr
385                 390                 395                 400

Ser Ser Asn Ser Lys Asn Tyr Leu Ala Trp Tyr Gln Gln Lys Pro Gly
                405                 410                 415

Gln Pro Pro Lys Leu Leu Ile Tyr Trp Ala Ser Thr Arg Glu Ser Gly
            420                 425                 430

Val Pro Asp Arg Phe Ser Gly Ser Gly Ser Gly Thr Asp Phe Thr Leu
        435                 440                 445

Thr Ile Ser Ser Leu Gln Ala Glu Asp Val Ala Val Tyr Tyr Cys Gln
    450                 455                 460

Gln Tyr Tyr Ser Thr Pro Tyr Ser Phe Gly Gln Gly Thr Lys Leu Glu
465                 470                 475                 480
```

```
Ile Lys Arg Ser Gly Ser Ala Trp Arg His Pro Gln Phe Gly Gly   *
            485                 490                 495
```

(2) INFORMATION FOR SEQ ID NO: 5:

(i) SEQUENCE CHARACTERISTICS:
        (A) LENGTH: 1031 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..1031

(xi) SEQUENCE DESCRIPTION: SEQ ID NO: 5:

```
ATG AAA AAG ACA GCT ATC GCG ATT GCA GTG GCA CTG GCT GGT TTC GCT        48
Met Lys Lys Thr Ala Ile Ala Ile Ala Val Ala Leu Ala Gly Phe Ala
 1               5                  10                  15

ACC GTA GCG CAG GCC GAC TAC AAG GAC GAT GAC GAC AAG GAT ATC GTG        96
Thr Val Ala Gln Ala Asp Tyr Lys Asp Asp Asp Asp Lys Asp Ile Val
                20                  25                  30

ATG ACC CAG TCT CCA GAC TCC CTG GCT GTG TCT CTG GGC GAG CGT GCC       144
Met Thr Gln Ser Pro Asp Ser Leu Ala Val Ser Leu Gly Glu Arg Ala
            35                  40                  45

ACC ATC AAT TGC AAG TCC AGC CAG AGT GTT TTA TAC AGC TCC AAC AGC       192
Thr Ile Asn Cys Lys Ser Ser Gln Ser Val Leu Tyr Ser Ser Asn Ser
         50                  55                  60

AAG AAC TAC CTG GCT TGG TAC CAG CAG AAA CCA GGT CAG CCT CCT AAG       240
Lys Asn Tyr Leu Ala Trp Tyr Gln Gln Lys Pro Gly Gln Pro Pro Lys
 65                  70                  75                  80

CTG CTC ATT TAC TGG GCA TCT ACC CGT GAA TCC GGC GTT CCT GAC CGT       288
Leu Leu Ile Tyr Trp Ala Ser Thr Arg Glu Ser Gly Val Pro Asp Arg
                 85                  90                  95

TTC AGT GGT AGC GGT TCT GGT ACA GAT TTC ACT CTC ACC ATC AGC AGC       336
Phe Ser Gly Ser Gly Ser Gly Thr Asp Phe Thr Leu Thr Ile Ser Ser
                100                 105                 110

CTC CAG GCT GAA GAT GTG GCA GTT TAT TAC TGC CAG CAG TAT TAC AGT       384
Leu Gln Ala Glu Asp Val Ala Val Tyr Tyr Cys Gln Gln Tyr Tyr Ser
            115                 120                 125

ACC CCG TAC TCC TTC GGT CAG GGT ACC AAA CTG GAA ATC AAA CGC TCC       432
Thr Pro Tyr Ser Phe Gly Gln Gly Thr Lys Leu Glu Ile Lys Arg Ser
        130                 135                 140

GGT AGC GGT GGC GGT GGT TCT GGT GGT GGT GGG AGC TCT GGT GGT GGC       480
Gly Ser Gly Gly Gly Gly Ser Gly Gly Gly Gly Ser Ser Gly Gly Gly
145                 150                 155                 160

TCT GGT GGT GGT AGC GAA AAC CTG TAC TTC CAG GGT GGT AGC GCC GAA       528
Ser Gly Gly Gly Ser Glu Asn Leu Tyr Phe Gln Gly Gly Ser Ala Glu
                165                 170                 175

GAA GTC ACG ATC AAA GCG AAC CTG ATC TTT GCA AAT GGT AGC ACA CAA       576
Glu Val Thr Ile Lys Ala Asn Leu Ile Phe Ala Asn Gly Ser Thr Gln
                180                 185                 190

ACT GCA GAA TTC AAA GGT ACC TTC GAA AAA GCG ACC TCG GAA GCT TAT       624
Thr Ala Glu Phe Lys Gly Thr Phe Glu Lys Ala Thr Ser Glu Ala Tyr
            195                 200                 205

GCG TAT GCA GAT ACT TTG AAG AAA GAC AAT GGT GAA TAT ACT GTA GAT       672
Ala Tyr Ala Asp Thr Leu Lys Lys Asp Asn Gly Glu Tyr Thr Val Asp
        210                 215                 220

GTT GCA GAT AAA GGT TAC ACC CTG AAC ATC AAA TTC GCG GGT AAA GAA       720
Val Ala Asp Lys Gly Tyr Thr Leu Asn Ile Lys Phe Ala Gly Lys Glu
225                 230                 235                 240
```

```
GCG ACC AAC CGT AAC ACC GAC GGT TCC ACC GAC TAC GGT ATC TTA CAG                    768
Ala Thr Asn Arg Asn Thr Asp Gly Ser Thr Asp Tyr Gly Ile Leu Gln
            245                 250                 255

ATC AAC TCT CGT TGG GGT GGT CTG ACC AGC GCC GAA GAA GTC ACG ATC                    816
Ile Asn Ser Arg Trp Gly Gly Leu Thr Ser Ala Glu Glu Val Thr Ile
            260                 265                 270

AAA GCG AAC CTG ATC TTT GCA AAT GGT AGC ACA CAA ACT GCA GAA TTC                    864
Lys Ala Asn Leu Ile Phe Ala Asn Gly Ser Thr Gln Thr Ala Glu Phe
            275                 280                 285

AAA GGT ACC TTC GAA AAA GCG ACC TCG GAA GCT TAT GCG TAT GCA GAT                    912
Lys Gly Thr Phe Glu Lys Ala Thr Ser Glu Ala Tyr Ala Tyr Ala Asp
        290                 295                 300

ACT TTG AAG AAA GAC AAT GGT GAA TAT ACT GTA GAT GTT GCA GAT AAA                    960
Thr Leu Lys Lys Asp Asn Gly Glu Tyr Thr Val Asp Val Ala Asp Lys
305                 310                 315                 320

GGT TAC ACC CTG AAC ATC AAA TTC GCG GGT AAA GAA AGC GCT TGG CGT                   1008
Gly Tyr Thr Leu Asn Ile Lys Phe Ala Gly Lys Glu Ser Ala Trp Arg
                325                 330                 335

CAC CCG CAG TTC GGT GGT TAA TA                                                    1031
His Pro Gln Phe Gly Gly  *
            340
```

(2) INFORMATION FOR SEQ ID NO: 6:

(i) SEQUENCE CHARACTERISTICS:
        (A) LENGTH: 343 amino acids
        (B) TYPE: amino acid
        (D) TOPOLOGY: linear (ii) MOLECULE TYPE: protein (xi) SEQUENCE DESCRIPTION: SEQ ID NO: 6:

```
Met Lys Lys Thr Ala Ile Ala Ile Ala Val Ala Leu Ala Gly Phe Ala
 1               5                  10                  15

Thr Val Ala Gln Ala Asp Tyr Lys Asp Asp Asp Lys Asp Ile Val
                20                  25                  30

Met Thr Gln Ser Pro Asp Ser Leu Ala Val Ser Leu Gly Glu Arg Ala
            35                  40                  45

Thr Ile Asn Cys Lys Ser Ser Gln Ser Val Leu Tyr Ser Ser Asn Ser
    50                  55                  60

Lys Asn Tyr Leu Ala Trp Tyr Gln Gln Lys Pro Gly Gln Pro Pro Lys
65                  70                  75                  80

Leu Leu Ile Tyr Trp Ala Ser Thr Arg Glu Ser Gly Val Pro Asp Arg
                85                  90                  95

Phe Ser Gly Ser Gly Ser Gly Thr Asp Phe Thr Leu Thr Ile Ser Ser
            100                 105                 110

Leu Gln Ala Glu Asp Val Ala Val Tyr Tyr Cys Gln Gln Tyr Tyr Ser
        115                 120                 125

Thr Pro Tyr Ser Phe Gly Gln Gly Thr Lys Leu Glu Ile Lys Arg Ser
    130                 135                 140

Gly Ser Gly Gly Gly Gly Ser Gly Gly Gly Gly Ser Ser Gly Gly Gly
145                 150                 155                 160

Ser Gly Gly Gly Ser Glu Asn Leu Tyr Phe Gln Gly Gly Ser Ala Glu
                165                 170                 175

Glu Val Thr Ile Lys Ala Asn Leu Ile Phe Ala Asn Gly Ser Thr Gln
            180                 185                 190

Thr Ala Glu Phe Lys Gly Thr Phe Glu Lys Ala Thr Ser Glu Ala Tyr
        195                 200                 205
```

```
Ala Tyr Ala Asp Thr Leu Lys Lys Asp Asn Gly Glu Tyr Thr Val Asp
    210                 215                 220
Val Ala Asp Lys Gly Tyr Thr Leu Asn Ile Lys Phe Ala Gly Lys Glu
225                 230                 235                 240
Ala Thr Asn Arg Asn Thr Asp Gly Ser Thr Asp Tyr Gly Ile Leu Gln
            245                 250                 255
Ile Asn Ser Arg Trp Gly Gly Leu Thr Ser Ala Glu Glu Val Thr Ile
            260                 265                 270
Lys Ala Asn Leu Ile Phe Ala Asn Gly Ser Thr Gln Thr Ala Glu Phe
        275                 280                 285
Lys Gly Thr Phe Glu Lys Ala Thr Ser Glu Ala Tyr Ala Tyr Ala Asp
    290                 295                 300
Thr Leu Lys Lys Asp Asn Gly Glu Tyr Thr Val Asp Val Ala Asp Lys
305                 310                 315                 320
Gly Tyr Thr Leu Asn Ile Lys Phe Ala Gly Lys Glu Ser Ala Trp Arg
            325                 330                 335
His Pro Gln Phe Gly Gly  *
            340
```

(2) INFORMATION FOR SEQ ID NO: 7:

(i) SEQUENCE CHARACTERISTICS:
        (A) LENGTH: 599 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..599

(xi) SEQUENCE DESCRIPTION: SEQ ID NO: 7:

```
ATG AAA AAG ACA GCT ATC GCG ATT GCA GTG GCA CTG GCT GGT TTC GCT        48
Met Lys Lys Thr Ala Ile Ala Ile Ala Val Ala Leu Ala Gly Phe Ala
1               5                   10                  15

ACC GTA GCG CAG GCC GAC TAC AAG GAC GAT GAC GAC AAG GGC GCC GAA        96
Thr Val Ala Gln Ala Asp Tyr Lys Asp Asp Asp Asp Lys Gly Ala Glu
                20                  25                  30

GAA GTC ACG ATC AAA GCG AAC CTG ATC TTT GCA AAT GGT AGC ACA CAA       144
Glu Val Thr Ile Lys Ala Asn Leu Ile Phe Ala Asn Gly Ser Thr Gln
            35                  40                  45

ACT GCA GAA TTC AAA GGT ACC TTC GAA AAA GCG ACC TCG GAA GCT TAT       192
Thr Ala Glu Phe Lys Gly Thr Phe Glu Lys Ala Thr Ser Glu Ala Tyr
        50                  55                  60

GCG TAT GCA GAT ACT TTG AAG AAA GAC AAT GGT GAA TAT ACT GTA GAT       240
Ala Tyr Ala Asp Thr Leu Lys Lys Asp Asn Gly Glu Tyr Thr Val Asp
65                  70                  75                  80

GTT GCA GAT AAA GGT TAC ACC CTG AAC ATC AAA TTC GCG GGT AAA GAA       288
Val Ala Asp Lys Gly Tyr Thr Leu Asn Ile Lys Phe Ala Gly Lys Glu
                85                  90                  95

GCG ACC AAC CGT AAC ACC GAC GGT TCC ACC GAC TAC GGT ATC TTA CAG       336
Ala Thr Asn Arg Asn Thr Asp Gly Ser Thr Asp Tyr Gly Ile Leu Gln
            100                 105                 110

ATC AAC TCT CGT TGG GGT GGT CTG ACC AGC GCC GAA GAA GTC ACG ATC       384
Ile Asn Ser Arg Trp Gly Gly Leu Thr Ser Ala Glu Glu Val Thr Ile
        115                 120                 125

AAA GCG AAC CTG ATC TTT GCA AAT GGT AGC ACA CAA ACT GCA GAA TTC       432
Lys Ala Asn Leu Ile Phe Ala Asn Gly Ser Thr Gln Thr Ala Glu Phe
```

```
                130             135             140
AAA GGT ACC TTC GAA AAA GCG ACC TCG GAA GCT TAT GCG TAT GCA GAT       480
Lys Gly Thr Phe Glu Lys Ala Thr Ser Glu Ala Tyr Ala Tyr Ala Asp
145                 150                 155                 160

ACT TTG AAG AAA GAC AAT GGT GAA TAT ACT GTA GAT GTT GCA GAT AAA       528
Thr Leu Lys Lys Asp Asn Gly Glu Tyr Thr Val Asp Val Ala Asp Lys
                165                 170                 175

GGT TAC ACC CTG AAC ATC AAA TTC GCG GGT AAA GAA AGC GCT TGG CGT       576
Gly Tyr Thr Leu Asn Ile Lys Phe Ala Gly Lys Glu Ser Ala Trp Arg
            180                 185                 190

CAC CCG CAG TTC GGT GGT TAA  TA                                       599
His Pro Gln Phe Gly Gly  *
        195             200

(2) INFORMATION FOR SEQ ID NO: 8:

(i) SEQUENCE CHARACTERISTICS:
        (A) LENGTH: 199 amino acids
        (B) TYPE: amino acid
        (D) TOPOLOGY: linear (ii) MOLECULE TYPE: protein (xi) SEQUENCE DESCRIPTION: SEQ ID NO: 8:

Met Lys Lys Thr Ala Ile Ala Ile Ala Val Ala Leu Ala Gly Phe Ala
1               5                   10                  15

Thr Val Ala Gln Ala Asp Tyr Lys Asp Asp Asp Lys Gly Ala Glu
            20                  25                  30

Glu Val Thr Ile Lys Ala Asn Leu Ile Phe Ala Asn Gly Ser Thr Gln
            35                  40                  45

Thr Ala Glu Phe Lys Gly Thr Phe Glu Lys Ala Thr Ser Glu Ala Tyr
    50                  55                  60

Ala Tyr Ala Asp Thr Leu Lys Lys Asp Asn Gly Glu Tyr Thr Val Asp
65                  70                  75                  80

Val Ala Asp Lys Gly Tyr Thr Leu Asn Ile Lys Phe Ala Gly Lys Glu
                85                  90                  95

Ala Thr Asn Arg Asn Thr Asp Gly Ser Thr Asp Tyr Gly Ile Leu Gln
                100                 105                 110

Ile Asn Ser Arg Trp Gly Leu Thr Ser Ala Glu Val Thr Ile
            115                 120                 125

Lys Ala Asn Leu Ile Phe Ala Asn Gly Ser Thr Gln Thr Ala Glu Phe
130                 135                 140

Lys Gly Thr Phe Glu Lys Ala Thr Ser Glu Ala Tyr Ala Tyr Ala Asp
145                 150                 155                 160

Thr Leu Lys Lys Asp Asn Gly Glu Tyr Thr Val Asp Val Ala Asp Lys
                165                 170                 175

Gly Tyr Thr Leu Asn Ile Lys Phe Ala Gly Lys Glu Ser Ala Trp Arg
            180                 185                 190

His Pro Gln Phe Gly Gly  *
        195

(2) INFORMATION FOR SEQ ID NO: 9:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: DNA (genomic)
```

(xi) SEQUENCE DESCRIPTION: SEQ ID NO: 9:

Asp Tyr Lys Asp Asp Asp Lys
1               5

(2) INFORMATION FOR SEQ ID NO: 10:

(i) SEQUENCE CHARACTERISTICS:
        (A) LENGTH: 470 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..470

(xi) SEQUENCE DESCRIPTION: SEQ ID NO: 10:

```
ATG AAA AAG ACA GCT ATC GCG ATT GCA GTG GCA CTG GCT GGT TTC GCT       48
Met Lys Lys Thr Ala Ile Ala Ile Ala Val Ala Leu Ala Gly Phe Ala
 1               5                  10                  15

ACC GTA GCG CAG GCC GAC TAC AAG GAC GAT GAC GAC AAG GAT ATC GTG       96
Thr Val Ala Gln Ala Asp Tyr Lys Asp Asp Asp Asp Lys Asp Ile Val
            20                  25                  30

ATG ACC CAG TCT CCA GAC TCC CTG GCT GTG TCT CTG GGC GAG CGT GCC      144
Met Thr Gln Ser Pro Asp Ser Leu Ala Val Ser Leu Gly Glu Arg Ala
        35                  40                  45

ACC ATC AAT TGC AAG TCC AGC CAG AGT GTT TTA TAC AGC TCC AAC AGC      192
Thr Ile Asn Cys Lys Ser Ser Gln Ser Val Leu Tyr Ser Ser Asn Ser
    50                  55                  60

AAG AAC TAC CTG GCT TGG TAC CAG CAG AAA CCA GGT CAG CCT CCT AAG      240
Lys Asn Tyr Leu Ala Trp Tyr Gln Gln Lys Pro Gly Gln Pro Pro Lys
 65                  70                  75                  80

CTG CTC ATT TAC TGG GCA TCT ACC CGT GAA TCC GGC GTT CCT GAC CGT      288
Leu Leu Ile Tyr Trp Ala Ser Thr Arg Glu Ser Gly Val Pro Asp Arg
                85                  90                  95

TTC AGT GGT AGC GGT TCT GGT ACA GAT TTC ACT CTC ACC ATC AGC AGC      336
Phe Ser Gly Ser Gly Ser Gly Thr Asp Phe Thr Leu Thr Ile Ser Ser
           100                 105                 110

CTC CAG GCT GAA GAT GTG GCA GTT TAT TAC TGC CAG CAG TAT TAC AGT      384
Leu Gln Ala Glu Asp Val Ala Val Tyr Tyr Cys Gln Gln Tyr Tyr Ser
       115                 120                 125

ACC CCG TAC TCC TTC GGT CAG GGT ACC AAA CTG GAA ATC AAA CGC TCC      432
Thr Pro Tyr Ser Phe Gly Gln Gly Thr Lys Leu Glu Ile Lys Arg Ser
   130                 135                 140

GGT AGC GCT TGG CGT CAC CCG CAG TTC GGT GGT TAA TA                   470
Gly Ser Ala Trp Arg His Pro Gln Phe Gly Gly  *
145                 150                 155
```

(2) INFORMATION FOR SEQ ID NO: 11:

(i) SEQUENCE CHARACTERISTICS:
        (A) LENGTH: 156 amino acids
        (B) TYPE: amino acid
        (D) TOPOLOGY: linear (ii) MOLECULE TYPE: protein (xi) SEQUENCE DESCRIPTION: SEQ ID NO: 11:

Met Lys Lys Thr Ala Ile Ala Ile Ala Val Ala Leu Ala Gly Phe Ala
 1               5                  10                  15

Thr Val Ala Gln Ala Asp Tyr Lys Asp Asp Asp Asp Lys Asp Ile Val

```
                    20                      25                      30
Met Thr Gln Ser Pro Asp Ser Leu Ala Val Ser Leu Gly Glu Arg Ala
            35                      40                      45
Thr Ile Asn Cys Lys Ser Ser Gln Ser Val Leu Tyr Ser Ser Asn Ser
        50                      55                      60
Lys Asn Tyr Leu Ala Trp Tyr Gln Gln Lys Pro Gly Gln Pro Pro Lys
65                      70                      75                      80
Leu Leu Ile Tyr Trp Ala Ser Thr Arg Glu Ser Gly Val Pro Asp Arg
                    85                      90                      95
Phe Ser Gly Ser Gly Ser Gly Thr Asp Phe Thr Leu Thr Ile Ser Ser
                100                     105                     110
Leu Gln Ala Glu Asp Val Ala Val Tyr Tyr Cys Gln Gln Tyr Tyr Ser
            115                     120                     125
Thr Pro Tyr Ser Phe Gly Gln Gly Thr Lys Leu Glu Ile Lys Arg Ser
        130                     135                     140
Gly Ser Ala Trp Arg His Pro Gln Phe Gly Gly   *
145                     150                     155
```

(2) INFORMATION FOR SEQ ID NO: 12:

(i) SEQUENCE CHARACTERISTICS:
        (A) LENGTH: 539 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..539

(xi) SEQUENCE DESCRIPTION: SEQ ID NO: 12:

```
ATG GAC TAC AAG GAC GAT GAC GAC AAG GGC GCC GAA GAA GTC ACG ATC        48
Met Asp Tyr Lys Asp Asp Asp Asp Lys Gly Ala Glu Glu Val Thr Ile
1               5                   10                  15

AAA GCG AAC CTG ATC TTT GCA AAT GGT AGC ACA CAA ACT GCA GAA TTC        96
Lys Ala Asn Leu Ile Phe Ala Asn Gly Ser Thr Gln Thr Ala Glu Phe
                20                  25                  30

AAA GGT ACC TTC GAA AAA GCG ACC TCG GAA GCT TAT GCG TAT GCA GAT       144
Lys Gly Thr Phe Glu Lys Ala Thr Ser Glu Ala Tyr Ala Tyr Ala Asp
            35                  40                  45

ACT TTG AAG AAA GAC AAT GGT GAA TAT ACT GTA GAT GTT GCA GAT AAA       192
Thr Leu Lys Lys Asp Asn Gly Glu Tyr Thr Val Asp Val Ala Asp Lys
        50                  55                  60

GGT TAC ACC CTG AAC ATC AAA TTC GCG GGT AAA GAA GCG ACC AAC CGT       240
Gly Tyr Thr Leu Asn Ile Lys Phe Ala Gly Lys Glu Ala Thr Asn Arg
65                  70                  75                  80

AAC ACC GAC GGT TCC ACC GAC TAC GGT ATC TTA CAG ATC AAC TCT CGT       288
Asn Thr Asp Gly Ser Thr Asp Tyr Gly Ile Leu Gln Ile Asn Ser Arg
                85                  90                  95

TGG GGT GGT CTG ACC AGC GCC GAA GAA GTC ACG ATC AAA GCG AAC CTG       336
Trp Gly Gly Leu Thr Ser Ala Glu Glu Val Thr Ile Lys Ala Asn Leu
                100                 105                 110

ATC TTT GCA AAT GGT AGC ACA CAA ACT GCA GAA TTC AAA GGT ACC TTC       384
Ile Phe Ala Asn Gly Ser Thr Gln Thr Ala Glu Phe Lys Gly Thr Phe
            115                 120                 125

GAA AAA GCG ACC TCG GAA GCT TAT GCG TAT GCA GAT ACT TTG AAG AAA       432
Glu Lys Ala Thr Ser Glu Ala Tyr Ala Tyr Ala Asp Thr Leu Lys Lys
        130                 135                 140
```

```
GAC AAT GGT GAA TAT ACT GTA GAT GTT GCA GAT AAA GGT TAC ACC CTG         480
Asp Asn Gly Glu Tyr Thr Val Asp Val Ala Asp Lys Gly Tyr Thr Leu
145                 150                 155                 160

AAC ATC AAA TTC GCG GGT AAA GAA AGC GCT TGG CGT CAC CCG CAG TTC         528
Asn Ile Lys Phe Ala Gly Lys Glu Ser Ala Trp Arg His Pro Gln Phe
                165                 170                 175

GGT GGT TAA TA                                                          539
Gly Gly  *
            180
```

(2) INFORMATION FOR SEQ ID NO: 13:

(i) SEQUENCE CHARACTERISTICS:
        (A) LENGTH: 179 amino acids
        (B) TYPE: amino acid
        (D) TOPOLOGY: linear (ii) MOLECULE TYPE: protein (xi) SEQUENCE DESCRIPTION: SEQ ID NO: 13:

```
Met Asp Tyr Lys Asp Asp Asp Lys Gly Ala Glu Glu Val Thr Ile
 1               5                  10                  15

Lys Ala Asn Leu Ile Phe Ala Asn Gly Ser Thr Gln Thr Ala Glu Phe
                20                  25                  30

Lys Gly Thr Phe Glu Lys Ala Thr Ser Glu Ala Tyr Ala Tyr Ala Asp
            35                  40                  45

Thr Leu Lys Lys Asp Asn Gly Glu Tyr Thr Val Asp Val Ala Asp Lys
        50                  55                  60

Gly Tyr Thr Leu Asn Ile Lys Phe Ala Gly Lys Glu Ala Thr Asn Arg
65                  70                  75                  80

Asn Thr Asp Gly Ser Thr Asp Tyr Gly Ile Leu Gln Ile Asn Ser Arg
                85                  90                  95

Trp Gly Gly Leu Thr Ser Ala Glu Glu Val Thr Ile Lys Ala Asn Leu
                100                 105                 110

Ile Phe Ala Asn Gly Ser Thr Gln Thr Ala Glu Phe Lys Gly Thr Phe
            115                 120                 125

Glu Lys Ala Thr Ser Glu Ala Tyr Ala Tyr Ala Asp Thr Leu Lys Lys
        130                 135                 140

Asp Asn Gly Glu Tyr Thr Val Asp Val Ala Asp Lys Gly Tyr Thr Leu
145                 150                 155                 160

Asn Ile Lys Phe Ala Gly Lys Glu Ser Ala Trp Arg His Pro Gln Phe
                165                 170                 175

Gly Gly  *
```

(2) INFORMATION FOR SEQ ID NO: 14:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: DNA (genomic)

(xi) SEQUENCE DESCRIPTION: SEQ ID NO: 14:

```
Ala Trp Arg His Pro Gln Phe Gly Gly
 1               5
```